United States Patent
McTavish et al.

(10) Patent No.: US 11,957,783 B2
(45) Date of Patent: Apr. 16, 2024

(54) TOPICAL IMMUNOSENSITIZERS TO TREAT VIRAL AND FUNGAL INFECTIONS

(71) Applicant: Squarex, LLC, Pine Springs, MN (US)

(72) Inventors: Hugh McTavish, Pine Springs, MN (US); Thomas Dag Horn, Boston, MA (US)

(73) Assignee: Squarex Pharmaceutical Corporation, Pine Springs, MN (US)

( * ) Notice: Subject to any disclaimer, the term of this patent is extended or adjusted under 35 U.S.C. 154(b) by 310 days.

(21) Appl. No.: 17/194,832

(22) Filed: Mar. 8, 2021

(65) Prior Publication Data

US 2021/0186863 A1 Jun. 24, 2021

Related U.S. Application Data

(63) Continuation of application No. PCT/US2018/050358, filed on Sep. 11, 2018.

(51) Int. Cl.
| | |
|---|---|
| *A61K 9/00* | (2006.01) |
| *A61K 31/122* | (2006.01) |
| *A61K 47/20* | (2006.01) |
| *A61P 31/12* | (2006.01) |

(52) U.S. Cl.
CPC .......... *A61K 9/0014* (2013.01); *A61K 31/122* (2013.01); *A61K 47/20* (2013.01); *A61P 31/12* (2018.01)

(58) Field of Classification Search
CPC ....... A61P 31/12; A61P 31/10; A61K 2039/58
See application file for complete search history.

(56) References Cited

U.S. PATENT DOCUMENTS

| | | | | |
|---|---|---|---|---|
| 2001/0051182 A1* | 12/2001 | Hopp | ...................... | A61K 9/703 |
| | | | | 424/195.18 |
| 2002/0128326 A1* | 9/2002 | Kaplan | .................. | A61K 47/26 |
| | | | | 514/763 |
| 2006/0088561 A1* | 4/2006 | Eini | ........................ | A61Q 19/00 |
| | | | | 424/769 |

OTHER PUBLICATIONS

He et al (Advanced Science, 2023, 2202519, pp. 1-16) (Year: 2023).*
Kim et al (Annals of Dermatology, 1990, vol. 2, pp. 55-57) (Year: 1990).*
Kang et al (Acta DermVenereol, 2005, vol. 85, pp. 529-530) (Year: 2005).*
Dooms-Goossens et al (Contact Dermatitis, 1995, vol. 33, pp. 73-77) (Year: 1995).*
Kang et al (Acta DermVenereol, 2005, vol. 85, pp. 529-530, evidence of date) (Year: 2005).*
Kim et al (KJPR Korean J Plant Res, vol. 10, 1997, pp. 231-234) (Year: 1997).*

* cited by examiner

*Primary Examiner* — Mark V Stevens
(74) *Attorney, Agent, or Firm* — Hugh McTavish

(57) ABSTRACT

A method is presented for treating viral and fungal infections by applying a topical immunosensitizer to the skin of a person infected with a virus or fungus and in need of treatment for the viral or fungal infection. Methods of improving anti-viral and anti-fungal immunity are also presented, and methods of increasing PBMC interferon gamma expression in response to a viral or fungal immune stimulus.

17 Claims, No Drawings

TOPICAL IMMUNOSENSITIZERS TO TREAT VIRAL AND FUNGAL INFECTIONS

BACKGROUND

Topical immunosensitizers, also known as topical contact sensitizers, are compounds that when applied to human skin, cause a delayed-type hypersensitivity response. Some examples are squaric acid dibutyl ester (SADBE), diphenylcycolpropeneone (DPCP), 1-chloro-2,4-dinitrobenzene (DNCB), 1-chloro-2,6-dinitrobenzene. All of these have been used to treat common warts by topical application to the warts. (Lee A N, Mallory S B. Contact immunotherapy with squaric acid dibutylester for the treatment of recalcitrant warts. *J Am Acad Dermatol.* 1999; 41(4):595-599. Silverberg N B, Lim J K, Paller A S, Mancini A J. Squaric acid immunotherapy for warts in children. *J Am Acad Dermatol.* 2000; 42(5 Pt 1):803-808. Buckley, D A, Du Vivier A W, 2001, The therapeutic use of topical contact sensitizers in benign dermatoses. *British Journal of Dermatology* 2001; 145: 385-405.)

New substances and methods to treat viral and fungal infections are needed.

SUMMARY

The inventors have conducted a human clinical trial in persons who are infected with HSV-1 (have antibodies against HSV-1) who by self-reporting have frequent herpes labialis outbreaks (6 or more in the previous 12 months), infrequent outbreaks (1 or 2 outbreaks in the previous 12 months), or no outbreaks in the previous 12 months. Blood was collected from the subjects and peripheral blood mononuclear cells (PBMCs) isolated from the blood and plated in vitro in medium with no immune stimulus (negative control), with heat-inactivated HSV-1 virus particles, with heat-inactivated cell extracts from HSV-1-infected cells, and with *Candida albicans* extract. *Candida albicans* is yeast that is ubiquitous and infects skin and mucous membranes of persons. It is usually well-controlled in immunocompetent persons. *Candida albicans* extract is used as a skin test antigen of immune function.

The PBMCs were tested for proliferation against HSV-1, HSV-1-infected cell extracts, and *Candida* extract, and tested for immune gene expression in negative control media and in the presence of the three stimuli. In addition, on day 1 after blood collection the subjects with frequent outbreaks were dosed topically on the arm once with squaric acid dibutyl ester (SADBE), a topical immunosensitizer that has been shown to reduce frequency of herpes labialis outbreaks, and their PBMCs were collected and tested 2 weeks and 8 weeks later.

Those with good immune control of their HSV-1 infection (fewer or zero herpes labialis outbreaks) differ from those with poorer immune control (more outbreaks) in these ways:
  Greater PBMC proliferation in vitro to HSV-1, HSV-1-infected cell extracts, and *Candida* extract.
  Higher expression of the interferon gamma (IFNG) gene in PBMCs in vitro stimulated with HSV-1 virus, HSV-1-infected cell extracts, and *Candida* extract.
  Higher expression of almost all other immune related genes that are upregulated by stimulation with HSV-1, HSV-1-infected cell extracts, and *Candida* extract; and lower expression of genes that are down-regulated.

Treatment of subjects with frequent outbreaks with a single topical dose of SADBE causes their PBMCs to become more like those of the subjects with infrequent or zero outbreaks 56 days after the a single topical treatment with SADBE in every one of these ways than they had been on day 1 before the treatment, not just in the two HSV-1 stimuli but also for the *Candida* extract stimulus. In fact, in the key measure of interferon gamma gene expression the PBMCs of the subjects with frequent outbreaks went from significantly lower than those with infrequent and zero outbreaks on day 1 to higher than those with infrequent and zero outbreaks on day 57 in all three stimuli.

So a single topical dose of SADBE not only improved immune function of those with frequent herpes labialis outbreaks in 8 weeks, it actually made their immune function at 8 weeks better than persons with good immune control of HSV-1 and thus good immune function. Importantly, it not only improved immune response to HSV-1 virus and HSV-1-infected cell extracts, but also to a fungal extract. This indicates that as little as one SADBE application to intact healthy skin improves immune response to fungi as well as viruses, and therefore to viruses generally and not just herpes simplex virus. Since SADBE is believed to have these effects because it is a topical immunosensitizer and causes a delayed-type hypersensitivity response (DTH), other topical immunosensitizers would also have these effects.

We have also previously shown that a single topical dose of SADBE applied to the arm extended time to next herpes labialis outbreak in persons with frequent outbreaks. This is reported in Example 2 below. Together with the in vitro data of better immune response against HSV-1 and a fungal stimulus, this shows the better immune response in vitro to HSV-1 correlates with better control of HSV-1 infection in vivo, and thus the better immune response in vitro to a fungal stimulus indicates and predicts better immune control of fungal infections and other viral infections in vivo.

One embodiment provides a method of treating a viral infection or fungal infection comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

Another embodiment provides a method of improving anti-fungal or anti-viral immunity comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

Another embodiment provides a method of increasing peripheral blood mononuclear cell (PBMC) expression of interferon gamma in response to a viral or fungal immune stimulus in a person, the method comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

Another embodiment provides a method of treating molluscum contagiosum comprising: applying a topical immunosensitizer to the skin of a person infected with molluscum contagiosum pox virus and in recognized need of treatment for molluscum contagiosum.

Another embodiment provides a medical use of a topical immunosensitizer to prepare a medicament effective to treat a viral or fungal infection in a person when administered by (a) applying the topical immunosensitizer to skin of a person infected with a virus or a fungus and in recognized need of treatment for the viral or fungal infection; wherein the applying step is done on the person no more than 6 times in a 12 month period; wherein the viral infection is not an HSV, HPV, or HIV infection.

Another embodiment provides a composition comprising a topical immunosensitizer for use in a method of treating a viral or fungal infection, the method comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

Another embodiment provides a medical use of a topical immunosensitizer to prepare a medicament effective to improve immune response to a viral infection or a fungal infection in a person in recognized need of treatment for the viral infection or fungal infection, wherein the viral infection is not a herpes simplex virus (HSV) infection or a human papilloma virus (HPV) infection or a human immunodeficiency virus (HIV) infection.

Another embodiment provides a composition comprising a topical immunosensitizer to prepare a medicament effective to treat a viral infection or a fungal infection in a person in recognized need of treatment for the viral infection or fungal infection, wherein the viral infection is not a herpes simplex virus (HSV) infection or a human papilloma virus (HPV) infection or a human immunodeficiency virus (HIV) infection.

Another embodiment provides a composition comprising a topical immunosensitizer for use in a method of improving anti-fungal or anti-viral immunity, the method comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human mmunodeficiency virus (HIV) infection.

Another embodiment provides a composition comprising a topical immunosensitizer for use in a method of increasing PBMC expression of interferon gamma in response to a viral or fungal immune stimulus in a person, the method comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

Another embodiment provides a composition comprising a topical immunosensitizer for use in a method of treating molluscum contagiosum, the method comprising: applying a topical immunosensitizer to the skin of a person infected with molluscum contagiosum pox virus and in recognized need of treatment for molluscum contagiosum.

DETAILED DESCRIPTION

Definitions

The term "topical immunosensitizer" as used herein has the same meaning as "topical contact sensitizer." The two terms mean any substance that when topically applied to human skin induces a localized delayed type hypersensitivity (DTH) response (as evidenced by local erythema at the site of administration that peaks in a delayed manner, for instance, at about 2 days after administration, rather than peaking within the first 24 hours of administration) in a majority of previously sensitized persons. An appropriate test is application of a test substance at a concentration of 2% w/v in acetone or DMSO in a volume of 0.2 ml to a skin area of 2 cm squared or less (test application), after prior application of the same substance in the same concentration and amount to the same person (sensitization application) in the period of 2-12 weeks prior to the test application. For a topical immunosensitizer, the test application will induce a localized DTH response in the majority of persons.

Statements of the Invention

1. A method of treating a viral infection or fungal infection comprising:
 applying a topical immunosensitizer to the skin of a person infected with a virus or fungus and in recognized need of treatment for the viral or fungal infection;
 wherein the applying step is done no more than 6 times in a 12 month period;
 wherein the viral infection is not a herpes simplex virus (HSV) infection or a human papilloma virus (HPV) infection or a human immunodeficiency virus (HIV) infection.

2. The method of statement 1 wherein the infection is a viral infection and the person is in recognized need of treatment for molluscum contagiosum.

3. The method of statement 1 wherein the infection is a fungal infection and the person is in recognized need of treatment for the fungal infection.

4. The method of statement 3 wherein the infection is a yeast infection or in a more specific embodiment is a *Candida* infection.

5. The method of statement 4 wherein the infection is a vaginal yeast infection.

6. The method of statement 3 wherein the person is in recognized need of treatment for oral thrush.

7. The method of any one of statements 1-6 wherein the infection is an infection of the skin or mucous membrane or causes lesions on the skin or mucous membrane.

8. The method of statement 7 wherein infection causes lesions on the skin and the applying step comprises applying the topical immunosensitizer to a skin lesion caused by the infection.

9. The method of statement 7 wherein the infection causes leasions on the skin and the applying step does not comprise applying the topical immunosensitizer to a skin lesion caused by the infection.

10. The method of any one of statements 1-9 wherein the applying step is done no more than 4 times in a 12 month period.

11. The method of any one of statements 1-9 wherein the method does not comprise any two incidences of the applying step within 14 days of each other, or within 6 weeks of each other, or within 8 weeks of each other.

12. The method of any one of statements 1-11 wherein the topical immunosensitizer causes delayed erythema on the skin at the application site in the person evidencing a delayed-type hypersensitivity response in the person.

13. The method of any one of statements 1-11 wherein the topical immunosensitizer does not cause delayed erythema on the skin at the application site in the person.

14. The method of any one of statements 1-13 wherein the topical immunosensitizer is squaric acid dibutyl ester (SADBE), a squaric acid ester, diphenylcycolpropenenone (DPCP), 1-chloro-2,4-dinitrobenzene (DNCB), 1-chloro-2, 6-dinitrobenzene, or squaric acid.

15. The method of any one of statements 1-13 wherein the topical immunosensitizer is an artificial compound (defined as not found in nature).

16. The method of statement 14 wherein the topical immunosensitizer is SADBE.

17. The method of any one of statements 1-16 wherein the topical immunosensitizer is dissolved in dimethylsulfoxide (DMSO).

18. A method of improving anti-fungal or anti-viral immunity comprising:
applying a topical immunosensitizer to the skin of a person infected with a virus or fungus and in recognized need of treatment for the viral or fungal infection;
wherein the applying step is done no more than 6 times in a 12 month period;
wherein the viral infection is not a herpes simplex virus (HSV) infection or a human papilloma virus (HPV) infection or a human immunodeficiency virus (HIV) infection.

19. A method of increasing peripheral blood mononuclear cell (PBMC) expression of interferon gamma in response to a viral or fungal immune stimulus in a person, the method comprising:
applying a topical immunosensitizer to the skin of a person infected with a virus or fungus and in recognized need of treatment for the viral or fungal infection;
wherein the applying step is done no more than 6 times in a 12 month period;
wherein the viral infection is not a herpes simplex virus (HSV) infection or a human papilloma virus (HPV) infection or a human immunodeficiency virus (HIV) infection.

20. The method of statement 19 wherein PBMC expression of interferon gamma in response to a viral or fungal immune stimulus is not increased 14 days after the applying step.

21. The method of statement 19 wherein PBMC expression of interferon gamma in vitro in response to *Candida* extract is increased more than 3-fold 8 weeks after the applying step.

22. The method of statement 19 wherein PBMC expression of interferon gamma in vitro in response to heat-inactivated HSV-1 virus particles is increased more than 3-fold 8 weeks after the applying step.

23. The method of any one of statements 18-22 wherein the infection is a viral infection and the person is in recognized need of treatment for molluscum contagiosum.

24. The method of any one of statements 18-22 wherein the infection is a fungal infection and the person is in recognized need of treatment for the fungal infection.

25. The method of statement 24 wherein the infection is a yeast infection or in a more specific embodiment is a *Candida* infection.

26. The method of statement 25 wherein the infection is a vaginal yeast infection.

27. The method of statement 24 wherein the person is in recognized need of treatment for oral thrush.

28. The method of any one of statements 18-24 wherein the infection is an infection of the skin or mucous membrane or causes lesions on the skin or mucous membrane.

29. The method of statement 28 wherein infection causes lesions on the skin and the applying step comprises applying the topical immunosensitizer to a skin lesion caused by the infection.

30. The method of statement 28 wherein the infection causes leasions on the skin and the applying step does not comprise applying the topical immunosensitizer to a skin lesion caused by the infection.

31. The method of any one of statements 18-30 wherein the applying step is done no more than 4 times in a 12 month period.

32. The method of any one of statements 18-30 wherein the method does not comprise any two incidences of the applying step within 14 days of each other, or within 6 weeks of each other, or within 8 weeks of each other.

33. The method of any one of statements 18-32 wherein the topical immunosensitizer causes delayed erythema on the skin at the application site in the person evidencing a delayed-type hypersensitivity response in the person.

34. The method of any one of statements 18-32 wherein the topical immunosensitizer does not cause delayed erythema on the skin at the application site in the person.

35. The method of any one of statements 18-34 wherein the topical immunosensitizer is squaric acid dibutyl ester (SADBE), a squaric acid ester, diphenylcycolpropenenone (DPCP), 1-chloro-2,4-dinitrobenzene (DNCB), 1-chloro-2, 6-dinitrobenzene, or squaric acid.

36. The method of any one of statements 18-34 wherein the topical immunosensitizer is an artificial compound (defined as not found in nature).

37. The method of statement 35 wherein the topical immunosensitizer is SADBE.

38. The method of any one of statements 18-37 wherein the topical immunosensitizer is dissolved in dimethylsulfoxide (DMSO).

39. A method of treating molluscum contagiosum comprising:
applying a topical immunosensitizer to the skin of a person infected with molluscum contagiosum pox virus and in recognized need of treatment for molluscum contagiosum.

40. The method of statement 39 wherein the applying step is done no more than 6 times in a 12 month period.

41. The method of statement 39 wherein the applying step is done more than 6 times in a 12 month period.

42. The method of statement 39 wherein the method comprises applying the topical immunosensitizer to a molluscum contagiosum skin lesion.

43. The method of statement 39 wherein the method does not comprise applying the topical immunosensitizer to a molluscum contagiosum skin lesion.

44. The method of any one of statements 39, 40, 42, and 43 wherein the applying step is done no more than 4 times in a 12 month period.

45. The method of any one of statements 39, 40, 42, and 43 wherein the method does not comprise any two incidences of the applying step within 14 days of each other, or within 6 weeks of each other, or within 8 weeks of each other.

46. The method of any one of statements 39-45 wherein the topical immunosensitizer causes delayed erythema on the skin at the application site in the person evidencing a delayed-type hypersensitivity response in the person.

47. The method of any one of statements 39-45 wherein the topical immunosensitizer does not cause delayed erythema on the skin at the application site in the person.

48. The method of any one of statements 39-47 wherein the topical immunosensitizer is squaric acid dibutyl ester (SADBE), a squaric acid ester, diphenylcycolpropenenone (DPCP), 1-chloro-2,4-dinitrobenzene (DNCB), 1-chloro-2,6-dinitrobenzene, or squaric acid.

49. The method of any one of statements 39-47 wherein the topical immunosensitizer is an artificial compound (defined as not found in nature).

50. The method of statement 48 wherein the topical immunosensitizer is SADBE.

51. The method of any one of statements 39-50 wherein the topical immunosensitizer is dissolved in dimethylsulfoxide (DMSO).

52. The method of any one of statements 1-51 wherein the method comprises applying the contact sensitizer to the inner aspect of an upper arm of the person.

53. A medical use of a topical immunosensitizer to prepare a medicament effective to treat a viral or fungal infection in a person when administered by (a) applying the topical immunosensitizer to skin of a person infected with a virus or a fungus and in recognized need of treatment for the viral or fungal infection; wherein the applying step is done on the person no more than 6 times in a 12 month period; wherein the viral infection is not an HSV, HPV, or HIV infection.

54. A composition comprising a topical immunosensitizer for use in a method of treating a viral or fungal infection, the method comprising:
applying a topical immunosensitizer to the skin of a person infected with a virus or fungus and in recognized need of treatment for the viral or fungal infection;
wherein the applying step is done no more than 6 times in a 12 month period;
wherein the viral infection is not a herpes simplex virus (HSV) infection or a human papilloma virus (HPV) infection or a human immunodeficiency virus (HIV) infection.

55. A medical use of a topical immunosensitizer to prepare a medicament effective to improve immune response to a viral infection or a fungal infection in a person in recognized need of treatment for the viral infection or fungal infection, wherein the viral infection is not a herpes simplex virus (HSV) infection or a human papilloma virus (HPV) infection or a human immunodeficiency virus (HIV) infection.

56. The medical use of statement 55 wherein the viral infection is a molluscum contagiosum pox infection.

57. A composition comprising a topical immunosensitizer to prepare a medicament effective to treat a viral infection or a fungal infection in a person in recognized need of treatment for the viral infection or fungal infection, wherein the viral infection is not a herpes simplex virus (HSV) infection or a human papilloma virus (HPV) infection or a human immunodeficiency virus (HIV) infection.

58. A composition comprising a topical immunosensitizer for use in a method of improving anti-fungal or anti-viral immunity, the method comprising:
applying a topical immunosensitizer to the skin of a person infected with a virus or fungus and in recognized need of treatment for the viral or fungal infection;
wherein the applying step is done no more than 6 times in a 12 month period;
wherein the viral infection is not a herpes simplex virus (HSV) infection or a human papilloma virus (HPV) infection or a human immunodeficiency virus (HIV) infection.

59. A composition comprising a topical immunosensitizer for use in a method of increasing PBMC expression of interferon gamma in response to a viral or fungal immune stimulus in a person, the method comprising:
applying a topical immunosensitizer to the skin of a person infected with a virus or fungus and in recognized need of treatment for the viral or fungal infection;
wherein the applying step is done no more than 6 times in a 12 month period;
wherein the viral infection is not a herpes simplex virus (HSV) infection or a human papilloma virus (HPV) infection or a human immunodeficiency virus (HIV) infection.

60. A composition comprising a topical immunosensitizer for use in a method of treating molluscum contagiosum, the method comprising:
applying a topical immunosensitizer to the skin of a person infected with molluscum contagiosum pox virus and in recognized need of treatment for molluscum contagiosum.

61. A medical use of a topical immunosensitizer to prepare a medicament effective to improve anti-fungal or anti-viral immunity in a person when administered by (a) applying the topical immunosensitizer to skin of a person infected with a virus or a fungus and in recognized need of treatment for the viral or fungal infection; wherein the applying step is done on the person no more than 6 times in a 12 month period; wherein the viral infection is not an HSV, HPV, or HIV infection.

62. A medical use of a topical immunosensitizer to prepare a medicament effective to increase peripheral blood mononuclear cell (PBMC) expression of interferon gamma in response to a viral or fungal immune stimulus in a person when administered to the person by (a) applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection.

63. A medical use of a topical immunosensitizer to prepare a medicament effective to treat molluscum contagiosum in a person when administered by (a) applying the topical immunosensitizer to skin of a person infected with molluscum contagiosum pox virus and in recognized need of treatment for molluscum contagiosum.

Description

The topical immunosensitizer in some embodiments of the methods, compositions, and medical uses is an irritating plant extract (e.g., extract of poison ivy or poison sumac), urushiol, a squaric acid ester, (e.g., squaric acid dibutyl ester (SADBE), squaric acid monobutyl ester (SAMBE), squaric acid diethyl ester, or squaric acid monoethyl ester), squaric acid, diphenylcyclopropenone (DPCP), 1-chloro-2,4-dinitrobenzene (DNCB), or 1-chloro-2,6-dinitrobenzene.

The structure of squaric acid is shown below.

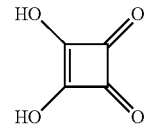

SADBE has the systemic name of 3,4-Dibutoxy-3-cyclobutene-1,2-dione. Its structure is shown below:

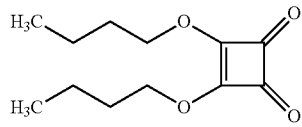 [SMILES: CCCCOc1c(OCCCC)c(=O)c1=O]

The topically applied immunosensitizer is typically applied as a solution in an organic solvent, e.g., acetone or dimethylsulfoxide. If soluble in water, it can instead by applied in an aqueous solution. It can also be applied in a cream, ointment, lotion, oil, etc. In specific embodiments of the invention, the topical immunosensitizer is dissolved in dimethylsulfoxide (DMSO).

It is not essential to induce a DTH response for the methods to work. In our clinical trial described in Example 2, the treated patients who did not develop a visible erythema at the site of application of SADBE nonetheless had a longer median time to the next HSV outbreak than patients receiving placebo.

Thus, in all methods described herein where the method involves inducing a DTH response, it can involve administering a topical immunosensitizer capable of inducing a DTH response without actually inducing a visible DTH response.

In specific embodiments of the methods, compositions, and medical uses of the invention, the viral or fungal infection may be an infection of the skin or mucous membrane or may cause lesions on the skin or mucous membrane. In other embodiments, the viral or fungal infection is not an infection of the skin or mucous membrane and does not cause lesions on the skin or mucous membrane.

We have shown that HSV outbreaks are delayed after a single dose of SADBE in DMSO applied to the arm of patients suffering from frequent HSV outbreaks. So it is not necessary to apply the immunosensitizer to a lesion or to diseased skin or mucous membrane. Thus, for instance, in some embodiments of treating fungal infections (e.g., yeast infections, e.g., vaginal yeast infections), the methods comprise applying the topical immunosensitizer to intact skin not affected by the fungus. In some embodiments, the methods do not comprise applying the topical immunosensitizer to lesions of skin or lesions of mucous membrane or to skin affected by the infection or mucous membrane affected by the infection. In other embodiments, the topical immunosensitizer is applied to lesions or to skin or mucous membrane affected by the infection.

Likewise, in some embodiments of viral infections, e.g., molluscum contagiosum pox virus infection, the methods comprise applying the topical immunosensitizer to intact skin not affected by the virus. In some embodiments, the methods do not comprise applying the topical immunosensitizer to lesions of skin or lesions of mucous membrane or to skin affected by the infection or mucous membrane affected by the infection. For instance, in some embodiments of treating molluscum contagiosum, the methods do not comprise applying the topical immunosensitizer to molluscum contagiosum lesions. In other embodiments, the topical immunosensitizer is applied to lesions, e.g., molluscum contagiosum lesions, or to skin or mucous membrane affected by the infection. But it is not necessary to apply the topical immunosensitizer to all lesions on the person.

In some embodiments of the methods, compositions, and medical uses, the composition comprising the immunosensitizer is applied to the inner aspect of the upper arm. The inner aspect of the upper arm refers to the surface of the upper arm that is in contact with the chest when a person holds their arms relaxed at their sides. This is where the initial dose of topical immunosensitizer was applied in the clinical trial described in Example 2, where efficacy was proven. The inner aspect of the upper arm is a favorable spot for application of the substance because the application may cause a rash, and the inner aspect of the upper arm is usually hidden by clothing, so any rash is not unsightly or embarrassing. It also is near a major lymph node in the armpit, and that may be part of the reason for the efficacy. So it may be the inner aspect of the upper arm is a particularly favorable spot to apply the drug for efficacy purposes, as well as being a hidden spot on the body in case a rash develops.

Another embodiment provides a method of increasing peripheral blood mononuclear cell (PBMC) expression of interferon gamma in response to a viral or fungal immune stimulus in a person, the method comprising: applying a topical immunosensitizer to the skin of a person infected with a virus or fungus and in recognized need of treatment for the viral or fungal infection; wherein the applying step is done no more than 6 times in a 12 month period; wherein the viral infection is not a herpes simplex virus (HSV) infection or a human papilloma virus (HPV) infection or a human immunodeficiency virus (HIV) infection; wherein the applying step increases PBMC expression of interferon gamma in response to the viral or fungal immune stimulus in the person 8 weeks after the applying step.

In one embodiment the applying step of any of the methods increases PBMC expression of interferon gamma in vitro in response to the virus or fungus more than 2-fold 8 weeks after the applying step.

EXAMPLE 1

Immune Characteristics of Hsv-1-Positive Subjects with Infrequent or No Episodes of Herpes Labialis Versus Those with Frequent Episodes, and Effect of Dosing of Sadbe on Immune Characteristics of Subjects with Frequent Episodes Abstract Peripheral blood mononuclear cells (PBMCs) were collected from persons positive for IgG against herpes simplex virus type 1 (HSV-1) and having frequent, infrequent, or no herpes labialis outbreaks. The PBMCs were tested for proliferation against HSV-1 and immune gene expression in the presence of HSV-1. In addition, on day 1 after blood collection the subjects with frequent outbreaks were dosed topically on the arm once with squaric acid dibutyl ester (SADBE), which has been shown to reduce frequency of herpes labialis outbreaks, and their PBMCs were collected and tested 2 weeks and 8 weeks later.

Those with good immune control of their HSV-1 infection (fewer or zero herpes labialis outbreaks) differ from those with poorer immune control (more outbreaks) in these ways:
  Greater PBMC proliferation in vitro to HSV-1.
  Higher expression of the IFNG gene and lower expression of the IL5 gene in PBMCs in vitro stimulated with HSV-1 virus.
  Higher expression of almost all other immune related genes that are upregulated by stimulation with HSV-1 and lower expression of genes that are down-regulated.

Treatment of subjects with frequent outbreaks with a single topical dose of SADBE causes their PBMCs to become more like those of the subjects with infrequent or zero outbreaks 56 days after the a single topical treatment with SADBE in every one of these ways than they had been on day 1 before the treatment.

Introduction

Herpes labialis is a common condition characterized by blisters or erosions on the lips and skin around the mouth and nose (Woo 2007; Sarnoff 2014; Opstelten 2008). Primary oral infection with the herpes simplex virus (HSV) typically occurs at a young age and is asymptomatic and not associated with significant morbidity. Most cases are caused by herpes simplex virus type 1 (HSV-1), but 10-15% of cases are caused by HSV-2 with this percentage reportedly increasing (Sarnoff 2014). In a population survey in the U.S., 76% of adults were positive for IgG antibodies against HSV-1 (Parks 2007). A population survey of over 10,000 randomly selected adults in France found 14.8% had a herpes labialis episode in the previous 12 months, and of those with herpes labialis, 12.94% had 6 or more occurrences in the last 12 months (Lorette 2006).

The natural history of HSV-1 infection leading to herpes labialis is that the virus initially infects oral mucosa tissue, and then migrates to sensory neurons and establishes latency in sensory neurons, typically the trigeminal ganglion. The virus is later activated from latency by events including fever, stress, cold or flu infection, immunosuppression, and sunlight. Upon activation, the virus migrates down sensory neurons to epithelial cells, typically on the vermillion border of the lip, and causes cell lysis and outbreaks as dermal lesions there (Nicoll 2012). Outbreaks typically last 1-2 weeks. The frequency and severity of outbreaks is thought to be dependent on the effectiveness of immune control of the virus (McKenna 2001; Daheshia 1998).

In a previous placebo-controlled clinical trial, topical application of a 2% solution of squaric acid dibutyl ester (SADBE) in dimethylsulfoxide (DMSO), applied once to the arm of persons who self-reported 6 or more herpes labialis outbreaks over the previous 12 months, was found to significantly delay the next outbreak. The median time to the next outbreak for the placebo group was 40 days vs more than 122 days for the 2.0% SADBE group, which difference was highly significant (P=0.009) (Palli 2017). SADBE is a topical immunosensitizer that induces a delayed-type hypersensitivity response and is commonly used in the treatment of verruca vulgaris and alopecia areata (Lee 1999; Silverberg 2000, Rokhshar 1998).

In this study we first sought to determine differences in immune function in general, and in immune response to HSV-1 in particular, between persons who are infected with HSV-1 and have frequent herpes labialis episodes (6 or more outbreaks in previous 12 months, group A) as compared to persons who are infected with HSV-1 and have infrequent herpes labialis episodes (1 or 2 outbreaks in previous 12 months, group B) or infected with HSV-1 and have no herpes labialis episodes (0 outbreaks in previous 12 months, group C). Second, we also sought to determine the effects on the immune system in general and on immune response to HSV-1 virus in particular of a single topical application of 2% SADBE in DMSO to the arm.

The outcomes measured were:
 Blood levels:
  Blood cell counts, including lymphocytes, T cells, B cells, CD4, CD8, and natural killer cells.
  Serum anti-HSV-1 IgG quantitative levels.
  Plasma cytokine levels.
 Peripheral blood mononuclear cell (PBMC) proliferation in vitro in response to:
  HSV-1-infected cell extracts (heat inactivated)
  HSV-1 virus, cell-free (heat inactivated)
  *Candida albicans* extract (a common infectious organism whose extract is used to measure general immune function).
 Cytokine and immune-function gene expression of PBMC in vitro in response to
  Medium only negative control
  HSV-1-infected cell extracts (heat inactivated)
  HSV-1 virus, cell-free (heat inactivated)
  *Candida albicans* extract These assays were performed on all subjects in each of the groups on day 1. The subjects in group A, the frequent cold sore sufferers, were then treated with a single dose of SADBE topically on the arm after their blood collection on day 1. They returned for blood collections on days 15 and 57 to measure the same outcomes.

Materials and Methods

This study was a clinical trial titled: "A Phase 1 Study of the Immune Response to Herpes Simplex Virus Type 1 (HSV-1) and General Immune Health in Subjects Infected with HSV-1" conducted at Prism Clinical Research, St. Paul, MN, USA.

Subjects.

Subjects ages 18-64 who were positive for anti-HSV-1 IgG were recruited in three groups of 12 subjects each. The groups were approximately age matched and gender composition matched. The groups self-reported different numbers of herpes labialis episodes over the prior 12 months: (A) 6 or more herpes labialis outbreaks over the previous 12 months, (B) 1 or 2 herpes labialis outbreaks over the previous 12 months, and (C) zero herpes labialis outbreaks over the previous 12 months.

Procedures.

After a screening visit at which blood was drawn to test for IgG antibody against HSV-1 and subjects were interviewed for inclusion/exclusion criteria, selected subjects returned for blood draws on day 1. After the blood draw on day 1, subjects in group A only were dosed with SADBE. A petrolatum donut was applied with a cotton swab to form about a 1 cm diameter donut on skin on the inner aspect of the upper arm. Then a separate cotton swab was dipped in a 2% SADBE solution (w/v) in DMSO, and the swab was then used to apply about 10-20 mg of solution over about a 1 cm diameter circle within the petrolatum donut. Immediately after application, the application site was covered with TEGADERM. Subjects were advised to remove the TEGADERM and rinse and wipe the spot three hours later. The group A subjects then returned for blood draws on days 15 and 57 and were queried about adverse events on those dates.

At this study visit where blood was drawn it was tested for blood cell counts, various cytokine levels, and anti-HSV-1 IgG quantitative levels.

Blood was also collected for isolation of peripheral blood mononuclear cells (PBMC) and the PBMC were subsequently isolated the same day and plated the same day for proliferation assays and gene expression assays as described below.

PBMC were isolated using SepMate PBMC isolation tubes (Stem Cell Technologies, Vancouver, Canada) and Ficoll-Paque according to the manufacturer's instructions. PBMC were isolated and suspended in negative control medium at 2 million cells/ml. PBMC suspension (100 μL) was added to 100 μL of medium in quadruplicate in 96-well plates. The plates were prepared in advance and stored at −70° C. The wells were in five different conditions in quadruplicate with these final concentrations after addition of the 100 μL of PBMC suspension in negative control medium.
1. Negative control in medium (RPMI with glutamine and pen/strep, supplemented with 10% human A/B serum).
2. Medium plus 16 μg/ml protein from heat-inactivated HSV-1-infected Vero cell extracts.
3. Medium plus heat-inactivated HSV-1 cell-free virus at a final 7.5 million pfu/ml.
4. Medium plus Candida cell extract. (Greer item number M15A50, 20,000 pnu/ml allergenic extract mixed molds Candida albicans, was diluted 1/50 into medium).
5. Positive control, medium plus 10 μg/ml concanavalin A.

Two plates were created for each subject at each collection point. One plate was incubated for 2 days at 37° C. in a humidified 5% $CO_2$ atmosphere and then RNA was isolated from the pooled contents of the 4 wells of a given condition for a specific patient, and the RNA was stored at −70° C. and subsequently used for quantitative real time PCR analysis of gene expression of 41 immune-related genes.

A second plate was incubated for 4 days. On the 4th day 1 μCi of tritiated thymidine in 50 μl of fresh negative control medium was added to each well. After 22 hours incubation the cells were harvested onto a filter mat and each well counted by scintillation counting for tritium incorporation into DNA as a quantitative measure of cell division.

HSV-1-Infected Cell Extracts:

HSV-1-infected cell extracts were made by plating 10 million Vero cells in each of three T-75 flasks on day 0, withdrawing all medium and adding cell-free HSV-1 virus (KOS strain) (ATCC strain VR-1493) in 2 ml medium on day 1 (at a multiplicity of infection of about 3), incubating for 2 hours to allow infection, and then adding 13 ml of medium. Then on day 2 cells were scraped off with cell scrapers, pelleted by low-speed centrifugation, washed twice in PBS, resuspended in 2 ml water total for all 3 flasks pooled in one snap-cap tube, and sonicated in a bath type sonicator in an ice-water bath for 4 minutes. The resultant cell extracts were stored at −70° C.

Cell-Free HSV-1 Virus.

Cell-free HSV-1 virus was made by plating 10 million Vero cells per T-75 flask on day 0. On day 1 medium was removed, and about 10 million virus was added in 2 ml of medium per flask for a multiplicity of infection of about 1. This was incubated with rocking every 2 minutes for 1-2 hours to allow viral adsorption to the cells. On day 4, the flasks were shaken to detach cells, the contents were then withdrawn and centrifuged at 1400×g for 10 minutes to pellet cells and cell debris. The supernatant was collected and centrifuged at 23,000×g for 2 hours to pellet virus. The pellet was resuspended in 1 ml of Vero medium for each T-75 harvested, and then frozen at −70° C. Virus prepared this way was found to have about $2.4 \times 10^9$ pfu/ml.

Both the HSV-1-infected cell extracts and the cell-free HSV-1 virus were heated at 70° C. for 30 minutes before adding them to the PBMC plates to heat inactivate virus to prevent it killing the PBMCs in the plates.

HSV-1 Pfu Determination.

To determine the number of plaque forming units of HSV-1 per ml in a preparation, the following assay was done. Vero cells were plated at 5,000 cells per well in a 96-well plate on day 0. On day 1 the HSV-1 preparation was diluted in a series of 2.5-fold dilutions from a 10,000-fold dilution. Forty μl of each of the dilutions was added to wells in triplicate, and the plate incubated 6 more days at 37° C. in a 5% $CO_2$ humidified atmosphere. Then 50 μl of a 4:1 mixture of medium and Dojindo cell counting kit reagent was added to each well, and the absorbance at 450 nm read until the O.D. in negative control wells with no virus added reached 2.5. The greatest dilution with loss of more than 50% of cell viability in wells was considered to have 1 pfu added to the well.

Real Time PCR

RNA Isolation and Pre-Amplification.

As noted above, after 2 days of growth of the PBMC in a 37° C. humidified 5% $CO_2$ incubator in a 96-well plate, four wells of a single condition (negative control, positive control, heat-inactivated HSV-1, HSV-1-infected cell extracts, or Candida extract) with cells from a single subject (200 μL in each well) were pooled, and the RNA was immediately isolated with Trizol reagent and chloroform by Qiagen RNeasy MiniElute clean up kit Qiagen cat #74204, according to manufacturer's instructions into a final volume of 13 μL, and then flash frozen on powdered dry ice, and stored at −70° C. in aliquots of 3 μL for RNA quantification and 10 μL for PCR analysis.

RNA was preamplified with the Qiagen RT2 PreAMP cDNA synthesis kit (Ref. 330451) and custom RT2 PreAmp primer mix (Ref. 330141) starting with about 50 ng RNA according to the procedure of RT preamp cDNA synthesis handbook date March 2011, pages 17-20. The amplification reactions (final 120 μL) were frozen at −70° C. and used for qPCR analysis the next day.

qPCR qPCR was done with the Qiagen RT PCR profiler gene analysis kit (catalog number 330451) using RT2 Sybr Green Rox qPCR Mastermix (24) (Part 330523) and Custom RT2 PCR array plates (Ref. 330171). For this 675 μL 2×RT2 SYBR green mastermix, 51 μL pre-AMP synthesis reaction, and 623 μL RNase free water were mixed, and then 25 μL of the mixture was added to 48 wells on the left or right half of the custom PCR plate. The PCR instrument was Applied Biosystems 7900HT fast real time PCR. The program was 95 C for 10 minutes; then 40 cycles of 95° C. for 15 seconds, 60° C. for 1:00; then stage 3 denaturation stage of 95° C. for 15 seconds, 60° C. for 15 seconds, and 95° C. for 15 seconds. The detector and reporter dye was Sybr, passive reference was Rox. For data analysis a manual Cq of 0.5 was used for all runs.

Control genes were ACTB, RPLPO, GAPDH. There were 41 test genes involved in immune function, and three wells for reverse transcriptase control, genomic DNA control, and positive PCR control. A fixed threshold level of 0.5 was used for all plates, and the threshold cycle (Ct) was calculated for each well as the cycle when the signal crossed the threshold.

Results

Subjects:

At the screening visit, subjects were asked an open-ended question of how many cold sore episodes, herpes labialis episodes, they had experienced in the previous 12 months. If they answered a number of 6 or more, they were eligible for group A. Group A was recruited first, and then groups B and C were recruited to be approximately age and sex matched to group A. Patients were eligible for group B if they answered that they had experienced 1 or 2 outbreaks in the prior 12 months, and were eligible for group C if they answered that they had experienced zero outbreaks in the previous 12 months. At the screening visit, blood was drawn from each subject, and to be accepted into the study the subject's serum had to test positive for the presence of anti-HSV-1 IgG, indicating that the subject was infected with HSV-1. The summary statistics of the subjects are in Table 1. There were 12 subjects in each group.

TABLE 1

Subject demographics.

| Group | Median Age | Age range | Sex |
|---|---|---|---|
| A (6 or more outbreaks) | 54.06 | 28.3 to 60.4 | 9 F/3 M |
| B (1 or 2 outbreaks) | 54.06 | 28.1 to 61.1 | 9 F/3 M |
| C (0 outbreaks) | 54.30 | 32.2 to 60.3 | 8 F/4 M |

Adverse Events

The study drug was well tolerated. Of the 12 subjects treated, two experienced stinging at the application site, and one had nausea that was ruled possibly related to the study drug. No rashes or delayed-type hypersensitivity reactions were reported, which is sometimes seen with SADBE.

PBMC Proliferation In Vitro.

The relative proliferation for each test condition was calculated as (avg. CPM test condition−avg. CPM negative control)/(avg. CPM positive control−avg. CPM negative control). The average CPM is the average tritium counts per minute of the 4 wells in a given test condition for a given collection point of a given patient. To calculate the normalized proliferation to all three stimuli, each data point was converted to a percentage proliferation relative to the average proliferation to that stimulus in group C or group A day 57, whichever was being compared to.

Table 2 shows the relative PBMC proliferation of subjects in groups A, B, and C. It can be seen that for all three stimuli tested PBMCs from the subjects with zero outbreaks proliferated more than those from subjects with 6 or more outbreaks. The subjects with 1 or 2 outbreaks were intermediate between the other two groups for all three stimuli. None of the differences for the individual stimuli reached statistical significance, but the difference in normalized values of all three stimuli together for group C vs. group A was almost significant (p=0.07).

TABLE 2

Relative proliferation of PBMCs collected from frequent cold sore sufferers (group A), infrequent cold sore sufferers (group B), and persons with zero cold sores in the prior 12 months (group C).

| | Percent proliferation (±Standard error) | | | |
|---|---|---|---|---|
| Stimulus | Group A, ≥6 outbreaks (n = 12) | Group B, 1, or 2 outbreaks (n = 12) | Group C, zero outbreaks (n = 12) | Group C v. Group A, p value, unpaired t test |
| HSV-1-infected cell extracts (n = 12) | 16.73 (±3.94) | 19.26 (±5.57) | 20.19 (±4.47) | p = 0.57 |
| HSV-1 virus (n = 12) | 8.26 (±1.98) | 11.71 (±2.98) | 12.70 (±3.05) | p = 0.24 |
| *Candida* extract (n = 12) | 4.47 (±1.53) | 4.85 (±1.51) | 7.83 (±2.19) | p = 0.22 |
| Normalized all three stimuli (n = 36) | 68.33% (±10.42) | 83.21% (±13.53) | 99.98% (±13.92) | p = 0.073 |

The same analysis was performed after removing the individual data points for each group with each stimulus that had the highest and lowest proliferation percentages. This decreased the P values for each stimulus in comparing group C to group A and for the normalized result of all three stimuli the C vs. A result became statistically significant. The result is shown in Table 3.

TABLE 3

Relative proliferation of PBMCs collected from frequent cold sore sufferers (group A), infrequent cold sore sufferers (group B), and persons with zero cold sores in the prior 12 months (group C), with the data point of the individual in each group with highest and lowest proliferation removed.

| | Percent proliferation (±Standard error) | | | |
|---|---|---|---|---|
| Stimulus | Group A, ≥6 outbreaks (n = 10) | Group B, 1, or 2 outbreaks (n = 10) | Group C, zero outbreaks (n = 10) | Group C v. Group A, p value, unpaired t test |
| HSV-1-infected cell extracts (n = 10) | 14.77 (±2.94) | 15.52 (±3.01) | 18.52 (±3.48) | p = 0.42 |

TABLE 3-continued

Relative proliferation of PBMCs collected from frequent cold sore sufferers (group A), infrequent cold sore sufferers (group B), and persons with zero cold sores in the prior 12 months (group C), with the data point of the individual in each group with highest and lowest proliferation removed.

| | Percent proliferation (±Standard error) | | | |
|---|---|---|---|---|
| Stimulus | Group A, ≥6 outbreaks (n = 10) | Group B, 1, or 2 outbreaks (n = 10) | Group C, zero outbreaks (n = 10) | Group C v. Group A, p value, unpaired t test |
| HSV-1 virus (n = 10) | 7.44 (±1.33) | 10.65 (±2.40) | 11.27 (±1.98) | p = 0.125 |
| Candida extract (n = 10) | 3.63 (±1.10) | 4.13 (±1.09) | 7.08 (±1.91) | p = 0.13 |
| Normalized all three stimuli (n = 30) | 65.67% (±8.37) | 76.37% (±10.48) | 100.00% (±12.10) | p = 0.023* |

*Statistically significant, p < 0.05.

Immediately after the blood collection on day 1, the group A subjects (frequent cold sore sufferers) were treated with one dose of topical 2% SADBE in DMSO applied to the inner aspect of the subject's arm. They returned for blood collection on day 15 and day 57, two and 8 weeks after the single dose of drug. The relative proliferation of PBMC from the group A subjects collected on days 1, 15, and 57, in response to the stimuli, is shown in Table 4.

TABLE 4

Proliferation of PBMCs collected from group A subjects (frequent cold sore sufferers) on day 1, day 15, and day 57. After the blood collection on day 1 the subjects received one treatment with SADBE.

| Group A | PBMC Percent proliferation (±Standard error) | | | Day 57 v. Day 1 |
|---|---|---|---|---|
| (6 or more outbreaks) Stimulus | Day 1 (n = 12) | Day 15 (n = 12) | Day 57 (n = 12) | p value, paired t test |
| HSV-1-infected cell extracts (n = 12) | 16.73 (±3.94) | 15.43 (±2.88) | 16.96 (±2.62) | p = 0.94 |
| HSV-1 virus (n = 12) | 8.26 (±1.98) | 10.52 (±1.63) | 13.37 (±2.38) | p = 0.047* |
| Candida extract (n = 12) | 4.47 (±1.53) | 3.33 (±1.15) | 7.35 (±2.42) | p = 0.28 |
| Normalized all three stimuli (n = 36) | 73.75% (±11.56) | 71.65% (±9.08) | 99.97% (±13.11) | p = 0.072 |

*Statistically significant, p < 0.05.

For all three stimuli, the PBMCs on day 57 proliferated better than on day 1. On day 15 the proliferation had not increased. The day 57 vs. day 1 difference in proliferation in the presence of heat-inactivated HSV-1 virus particles was statistically significant and the day 57 vs. day 1 normalized result using of all three stimuli was almost significant.

If the data points for the individuals with the largest and smallest (or most negative) differences in proliferation between days 57 and 1 for each of the three stimuli are removed from the analysis, the P values decrease for all three stimuli and the difference becomes highly significant for the HSV-1 virus stimulus, and the normalized proliferation to all three stimuli was also highly significantly different at day 57 versus day 1 in group A (Table 5).

TABLE 5

Proliferation of PBMCs collected from group A subjects (frequent cold sore sufferers) on day 1 and day 57. After the blood collection on day 1 the subjects received one treatment with SADBE with the data points of the 2 subjects with the largest and smallest difference between day 57 and day 1 for each stimulus removed.

| Group A (6 or more outbreaks) with the data points of 2 subjects with the largest and smallest difference between day 57 and day 1 removed. | Percent proliferation (±Standard error) | | Day 57 v. Day 1 p value, PAIRED t test |
|---|---|---|---|
| | Day 1 (n = 10) | Day 57 (n = 10) | |
| HSV-1-infected cell extracts (n = 10) | 14.56 (±3.02) | 15.78 (±2.94) | p = 0.69 |
| HSV-1 virus (n = 10) | 7.57 (±2.30) | 12.88 (±2.10) | p = 0.007** |
| Candida extract (n = 10) | 2.69 (±0.96) | 3.19 (±1.01) | p = 0.12 |
| Normalized all three stimuli (n = 30) | 67.86% (±10.85) | 99.97% (±10.17) | p = 0.010** |

**Highly statistically significant, $p \leq 0.01$.

Blood Cell Counts, Serum Cytokine Levels, and Serum Anti-HSV-1 IgG Levels

Certain blood cell count parameters were measured in the study. Some of the blood cell counts of subjects are shown in Table 6. Differences vs. group A day 1 that are statistically significant are highlighted in bold underline.

TABLE 6

Blood cell counts of subjects.

| Units | Group and day | Group average | Group St. Dev. | p value* vs. A1 | Sample minus A1 | Sample/A1 |
|---|---|---|---|---|---|---|
| | | Absolute Count CD19 (B-Cells) | | | | |
| cells/mm^3 | A1 | 194.37 | 79.93 | | | |
| cells/mm^3 | A15 | 171.74 | 85.20 | 0.033 | −22.63 | 0.88 |
| cells/mm^3 | A57 | 192.52 | 74.12 | 0.885 | −1.85 | 0.99 |
| cells/mm^3 | B1 | 166.18 | 84.67 | 0.411 | −28.19 | 0.85 |
| cells/mm^3 | C1 | 202.72 | 88.72 | 0.811 | 8.35 | 1.04 |
| | | Helper/Cytotoxic Ratio | | | | |
| | A1 | 5.25 | 5.41 | | | |
| | A15 | 3.58 | 1.82 | 0.306 | −1.67 | 0.68 |
| | A57 | 4.35 | 3.05 | 0.331 | −0.90 | 0.83 |
| | B1 | 3.07 | 0.93 | 0.182 | −2.18 | 0.58 |
| | C1 | 3.15 | 0.94 | 0.199 | −2.10 | 0.60 |
| | | Percentage CD19 (B-Cells) | | | | |
| % | A1 | 12.25 | 3.51 | | | |
| % | A15 | 10.17 | 3.91 | 0.004 | −2.08 | 0.83 |
| % | A57 | 11.67 | 4.03 | 0.253 | −0.58 | 0.95 |
| % | B1 | 12.08 | 4.27 | 0.918 | −0.17 | 0.99 |
| % | C1 | 12.25 | 3.61 | 1.000 | 0.00 | 1.00 |
| | | Percentage CD3 (T-Cells) | | | | |
| % | A1 | 76.08 | 6.63 | | | |
| % | A15 | 77.50 | 5.32 | 0.215 | 1.42 | 1.02 |
| % | A57 | 78.67 | 4.55 | 0.037 | 2.58 | 1.03 |
| % | B1 | 71.67 | 5.59 | 0.091 | −4.42 | 0.94 |
| % | C1 | 77.83 | 4.41 | 0.454 | 1.75 | 1.02 |
| | | T-cell to B-cell ratio | | | | |
| | A1 | 6.81 | 2.41 | | | |
| | A15 | 9.22 | 4.86 | 0.023 | 2.41 | 1.35 |
| | A57 | 7.50 | 2.56 | 0.099 | 0.69 | 1.01 |
| | B1 | 7.13 | 3.95 | 0.813 | 0.32 | 1.05 |
| | C1 | 7.13 | 2.77 | 0.762 | 0.32 | 1.05 |

*p values are from two-tailed unpaired t-test for groups B and C vs. A and from two-tailed paired t-test for days 15 and 57 vs. day 1 in group A.
n = 12 in each group.

B cell absolute count and percentage B cells were both significantly lower at day 15 in group A versus day 1, but were largely recovered at day 57. There was no significant difference in groups B and C in that parameter vs. group A. Percentage T cells was significantly higher at day 57 vs. day 1 in group A. The T to B cell ratio was significantly increased at day 15 vs. day 1 in group A and remained increased but not significantly at day 57.

The helper to cytotoxic cell ratio was lower in C and B vs. A day 1 and the p value is less than 0.20 for both comparisons of C vs. A and B vs. A. If groups B and C are pooled, the p value for groups B+C vs. A day 1 is 0.065, almost significant. The helper to cytotoxic ratio was also lower on day 57 than day 1 in group A, although the difference was not significant. Although the change in group A on day 57 was not statistically significant, this is another change to make group A more like those with better immune control of HSV-1 56 days after SADBE treatment.

Likewise, the T cell to B cell ratio was higher in group A on days 57 and 15 than on day 1, and the day 15 vs. day 1 comparison is statistically significant. The T/B cell ratio was not different between groups B or C versus group A on day 1.

There are no statistically significant differences in the cell count data for groups B or C vs. group A day 1, but it appears the helper to cytotoxic cell ratio (CD4+/CD8+) was lower in groups B and C than in group A on day 1, and that it moves in the direction of group A becoming more like groups C and B after dosing with SADBE, with the ratio lower on days 57 and 15 than day 1 in group A.

Other blood cell parameters that were measured but are not shown in Table 6 were absolute count CD16+CD56 (NK cells), absolute count CD3 (T cells), absolute count CD4 (helper T cells), absolute count CD8 (cytotoxic T cells), absolute lymphocyte count, percentage CD16+CD56 (NK cells), percentage CD4 (helper T cells), and percentage CD8 (cytotoxic T cells). None of these measurements had any significant or near significant differences between group A day 1 and groups B or C or between group A day 15 or 57 and day 1.

Cytokines:
Mostly Undetectable Cytokines

Plasma cytokine levels of the following cytokines were measured and were below detection limit in most subjects in all groups (detection limits in parentheses): Interferon gamma (1.58 pg/ml), Interleukin 1 beta (0.8 pg/ml), interleukin 10 (0.02 pg/ml), Interleukin 12/IL23p40 (3.52 pg/ml), Interleukin 13 (0.75 pg/ml), Interleukin 17A (CTLA-8) (2.38 pg/ml), Interleukin 4 (4.83 pg/ml), Interleukin 5 (0.84 pg/ml), Interleukin 6 (4.27 pg/ml), Interleukin 8 (CXCL8) (0.37 pg/ml), and tumor necrosis factor alpha (0.68 pg/ml). None of these had more than 3 of 12 subjects in any group (A1, A15, A57, B, or C) with detectable levels. So no conclusions could be drawn about significant differences between groups on any single cytokine. The closest was with IL-5 where 3/12 group B subjects and 3/12 group C subjects vs. 0/12 group A day 1 subjects had detectable levels. Groups B and C pooled together have 6 of 24 subjects with detectable levels. 0 of 12 in group A on day 1. That comparison has a two-tailed p value of p=0.08, almost statistically significant.

However, taken together a pattern emerged that group B and especially group C have more subjects with detectable cytokines in general from among the cytokines listed above than group A on day 1. Pooled together group A had 4 of 132 detectable measurements on day 1, while group B had 11 of 132 (p=0.10 vs. group A) and group C had 17 of 132 (p=0.005 vs. group A). Also in almost all cases the detectable measurements in group C had higher values than those in group A on day 1.

Interleukin 2 and Interleukin 2 Receptor.

All subjects had detectable IL-2 and the large majority had detectable IL-2 receptor. The measurements of these two parameters are shown in Table 7.

TABLE 7

Levels of IL-2 and IL2R in plasma.

| Units | Group and day | Number of subjects with undetectable levels | Group average (n = 12) | Group St. Dev. | p value* vs. A day 1 | Sample minus A1 | Sample/A1 |
|---|---|---|---|---|---|---|---|
| | | | Interleukin 2 | | | | |
| pg/mL | A1 | 0 | 13.44 | 5.50 | | | |
| pg/mL | A15 | 0 | 12.90 | 5.47 | 0.679 | −0.54 | 0.96 |
| pg/mL | A57 | 0 | 11.30 | 5.13 | 0.164 | −2.13 | 0.84 |
| pg/mL | B1 | 0 | 11.05 | 4.53 | 0.258 | −2.39 | 0.82 |
| pg/mL | C1 | 0 | 14.95 | 12.15 | 0.698 | 1.51 | 1.11 |
| | | Interleukin 2 Receptor (CD25) (Lower limit of detection 9.19 pg/ml) | | | | | |
| pg/mL | A1 | 2 | 732.76 | 589.02 | | | |
| pg/mL | A15 | 1 | 899.81 | 728.86 | 0.216 | 167.04 | 1.23 |
| pg/mL | A57 | 0 | 706.52 | 477.90 | 0.582 | −26.24 | 0.96 |
| pg/mL | B1 | 3 | 1194.75 | 2024.93 | 0.456 | 461.99 | 1.63 |
| pg/mL | C1 | 0 | 1504.27 | 1693.02 | 0.150 | 771.50 | 2.05 |

*p values are from two-tailed unpaired t-test for groups B and C vs. A and from two-tailed paired t-test for days 15 and 57 vs. day 0 in group A.
n = 12 in each group.

For IL2R the detection limit was 9.19 pg/ml and the number of subjects who measured undetectable are listed. If a subject's IL2R was undetectable, the value of 9.19 pg/ml was used for that subject in detecting the average of the group. No subjects had undetectable IL2.

The pattern of group C having higher cytokine levels than group A at day 0 is seen with IL2R, but the difference was not statistically significant.

Anti-HSV-1 IgG

Anti-HSV-1 IgG was quantified in serum collected at each study visit. The levels are shown in Table 8.

TABLE 8

Levels of anti-HSV1 IgG.

| Units | Group and day | Group average (n = 12) | Group St. Dev. | p value vs A1* | Sample minus A1 | Sample/A1 |
|---|---|---|---|---|---|---|
| IV | A1 | 8.32 | 1.90 | | | |
| IV | A15 | 9.39 | 1.59 | 0.197 | 1.08 | 1.13 |
| IV | A57 | 7.58 | 1.56 | 0.158 | −0.73 | 0.91 |
| IV | B1 | 6.61 | 1.65 | 0.028 | −1.71 | 0.79 |
| IV | C1 | 7.16 | 1.90 | 0.151 | −1.15 | 0.86 |
| IV | C1 + B1 | 6.88 | 1.84 | 0.038 | −1.43 | 0.83 |

*p values are from two-tailed unpaired t-test for groups B and C vs. A and from two-tailed paired t-test for days 15 and 57 vs. day 1 in group A.
n = 12 in each group, except n = 24 for the pooled groups C + B.

Group B had significantly lower anti-HSV1 IgG antibody than group A at day 1 and groups B and C pooled together had a significantly lower level of anti-HSV1 IgG than group A at day 1. Group C also had a lower level of anti-HSV1 antibody than group A, although the difference was not statistically significant. And on day 57, group A's anti-HSV1

IgG level was lower than it had been on day 0 (P=0.16), which is a move by day 57 toward the characteristic of the groups with fewer herpes labialis outbreaks. Since the antibody level initially went up in group A from day 1 to day 15, the change from day 15 to day 57 in group A was a highly significant decrease in anti-HSV1 IgG (P<0.01).

Cytokine and Immune-Related Gene Expression qRT-PCR was conducted on RNA collected from cells after 2 days of culture in medium with no stimulus (negative control) or with HSV-1-infected cell extracts, HSV-1 virus, or with *Candida* fungal extract.

Table 9 shows the average fold regulation of each gene in the groups B and C subjects combined, those with zero or few outbreaks and thus better immune control of HSV-1. Fold-regulation is absolute gene expression in the stimulus divided by absolute gene expression in the negative control.

TABLE 9

Average fold-regulation of immune-related genes from PBMCs of 12 group C subjects (HSV-1-infected persons with zero herpes labialis outbreaks in the prior 12 months) and 12 group B subjects (1 or 2 outbreaks in prior 12 months) pooled. The 10 most highly up-regulated genes for each stimulus are in bold, and genes down regulated at 0.70 or below are left justified, underlined, and italicized.

| Gene Symbol | HSV1-infected cell extract (CE) | HSV-1 Virus | *Candida* |
|---|---|---|---|
| CCL2 | 20.64 | 14.18 | 2.91 |
| CCL3 | 12.88 | 4.28 | 3.86 |
| CCL7 | 119.40 | 70.35 | 8.92 |
| CCR5 | 3.97 | 2.14 | 0.73 |
| CD80 | 12.03 | 5.69 | 1.44 |
| CXCL10 | 537.13 | 419.29 | 5.94 |
| CXCL11 | 370.37 | 88.51 | 1.93 |
| CXCL2 | 3.16 | 2.14 | 3.72 |
| CXCL5 | 1.49 | 0.94 | 4.57 |
| CXCL9 | 188.90 | 111.09 | 6.95 |
| DDX58 | 5.81 | 4.24 | 1.23 |
| FOXP3 | 2.73 | 2.88 | 2.46 |
| GATA3 | 0.93 | *0.57* | *0.49* |
| ICAM1 | 3.88 | 2.50 | 0.96 |
| IFNA1 | 10.74 | 6.35 | 0.99 |
| IFNB1 | 4.41 | 2.45 | 0.84 |
| IFNG | 46.02 | 19.67 | 9.31 |
| IL10 | 3.63 | 1.56 | 1.44 |
| IL12A | 1.87 | 2.26 | 1.52 |
| IL12B | 0.73 | *0.60* | 3.38 |
| IL13 | 4.04 | 3.88 | 5.62 |
| IL15 | 3.48 | 3.15 | 1.23 |
| IL16 | *0.68* | *0.69* | *0.67* |
| IL1B | 3.82 | 1.84 | 11.21 |
| IL1R1 | 0.94 | *0.58* | 1.01 |
| IL1RN | 18.02 | 5.41 | 1.53 |
| IL2 | 30.96 | 8.04 | 9.78 |
| IL4 | 1.28 | 1.62 | 1.17 |
| IL5 | 1.04 | 1.39 | 1.08 |
| IL8 | 8.76 | 5.83 | 6.52 |
| JAK2 | 4.17 | 3.52 | 1.04 |
| LTA | 2.77 | 2.43 | 2.10 |
| LYZ | *0.10* | *0.26* | *0.25* |
| MX1 | 19.39 | 10.06 | 0.76 |
| NOD1 | 1.93 | 1.81 | 0.91 |
| SPP1 | 23.26 | 3.26 | 0.72 |
| STAT1 | 8.26 | 9.34 | 2.27 |
| STAT4 | 1.43 | 1.82 | 1.35 |
| TNF | 3.09 | 2.64 | 1.76 |
| TNFSF10 | 8.32 | 5.92 | 1.12 |
| TNFSF13B | 3.42 | 3.59 | *0.70* |

The gene regulation is somewhat more similar between HSV-1-infected cell extracts and HSV-1 virus than between either HSV-1 infected cell extracts and *Candida* fungal extract or HSV-1 virus and *Candida*. But for all three stimuli interferon gamma (IFNG) is among the most up-regulated genes. IL2, another Th1-produced cytokine, is also up regulated strongly with all three stimuli. The up-regulation was generally lesser in *Candida* extract than with HSV-infected cell extract or virus, possibly because the *Candida* components were not at a high concentration in the wells. CXCL9, 10, and 11 are all very highly upregulated with the two HSV stimuli and 9 and 10 were rather upregulated by *Candida* as well. Those genes are all induced by IFNG (Corbera-Bellalta 2016). CCL7 is also strongly upregulated by all three stimuli.

LYZ (lysozyme gene) is down-regulated by all three stimuli. That makes sense because it is an antibacterial enzyme and the three stimuli are viral and fungal.

MX1 is a gene involved in antiviral response (Haller 2007), and it is strongly upregulated by both HSV stimuli and down-regulated by *Candida*.

SPP1 is strongly upregulated by HSV-1-infected cell extracts, and to a lesser extent by virus, but down regulated by *Candida*. SPP1 is a cytokine that upregulates expression of IFNG and IL12. It is also a regulator of apoptosis (Minton 2017). Apoptosis of viral-infected cells is a key method of immune control of viral infections, which may explain why SPP1 is upregulated by the viral stimuli but not by *Candida* extract.

GATA3 is significantly down regulated by virus and *Candida* and slightly down regulated by HSV1-infected cell extracts. GATA3 induces differentiation of Th0 cells to the Th2 subtype and suppresses differentiation to the Th1 subtype (Wan 2014, Zhu 2006). Since it is down regulated by these stimuli, the stimuli tend to drive T cells to the Th1 subtype.

IL16 is down-regulated by all three stimuli.

Almost all the gene expression changes shown in Table 9 are statistically significant (p<0.05) and in particular all of the changes highlighted in either yellow or orange are statistically significant.

The two Th1 cytokines (Annunziato 2015, Spellberg 2001)—IFNG and IL2—are both among the most upregulated genes in all three stimuli, while the Th2 cytokines (Annunziato 2015, Spellberg 2001) tested—IL4, IL5, IL10, and IL13—are much less upregulated by the stimuli, if upregulated at all.

Differences in PBMC Gene Expression Between Groups with Frequent, Infrequent, or No Herpes Labialis Outbreaks (Groups A, B, and C), and Difference in PBMC Gene Expression in Group A after SADBE Treatment.

Tables 10-13 show the ratio of PBMC absolute gene expression in groups B (1 or 2 outbreaks) and C (zero outbreaks) relative to group A (6 or more outbreaks) and in groups B+C pooled relative to group A in each of the three stimulants and in unstimulated condition (negative control medium). The absolute gene expression is the gene expression of the test gene relative to the housekeeping genes in the same wells. What is shown in Tables 10-13 is the absolute gene expression in group B or C or B+C divided by the absolute gene expression in group A in the same condition.

Tables 10-13 also show the ratio of PBMC absolute gene expression in group A on day 57 to day 1. The gene expression in group A on day 15 is not shown because there were far more significant differences in gene expression on day 57 vs. day 1 than on day 15 vs. day 1 and the differences were generally larger.

Tables 10, 11, and 12 group the responses by stimulant. One column in each table shows the fold up-regulation of each of the 41 genes in the stimulant (HSV-infected cell extracts, heat-killed HSV virus, or *Candida* extract) versus in negative control (NC) in group B and C subjects pooled. The next 3 columns show the ratio of absolute gene expression (the gene expression in the stimulus normalized to housekeeping genes in the same assay from the same stimulated cells) in groups B, C, or B+C pooled versus group A subjects on day 1 (blood collected before dosing with SADBE). The right column shows the ratio of in absolute gene expression in the stimulus in group A subjects on day 57 versus on day 1. Statistically significant changes (p<0.05) are in bold.

The three columns to the left of the gene symbol indicate the comparison of direction of change in any significant changes in gene expression. Only statistically significant results are included. In each column, two types of changes are compared, and if the direction of both changes is the same (both are increases or both are decreases in gene expression) it is marked S, if the directions of the two changes are different, it is marked D. The changes compared are (1) (stimulus vs. negative control) compared to (group A day 57 vs. A day 1), (2) (stimulus vs. negative control) compared to (groups B, C, or B+C vs. group A day 1), and (3) (groups B, C, or B+C vs. group A day 1) compared to (group A day 57 vs. A day 1). For the (groups B, C, or B+C vs. group A day 1), a change was considered significant if it was significant for either group B, group C, or groups B+C pooled versus group A.

TABLE 10

Comparison of changes in gene expression between groups B/C vs. A day 1, group A day 57 vs. day 1, and groups B/C in stimulus vs. negative control (NC), for HSV-1-infected cell extracts (CE) as stimulus.

| Direction of significant changes in gene expression: same (S) or different (D) | | | HSV-1-infected cell extracts (CE) | | | | |
|---|---|---|---|---|---|---|---|
| Stimulus v NC and A57 v A1 | Stimulus v NC and B/C v A1 | B/C v A1 and A57 v A1 | Gene Symbol | fold-stimulation in CE vs. NC in groups B + C | ratio of absolute gene expression in group vs. group A1 | | ratio of absolute expression in A57 vs. A1 |
| | | | | | B | C | B + C | |
|   |   |   | CCL2    | 20.64   | 0.814 | 0.916 | 0.864 | 1.21 |
| S | S | S | CCL3    | 12.88 | 3.825 | 2.448 | 3.060 | 4.6 |
|   |   |   | CCL7    | 119.40 | 0.702 | 0.782 | 0.741 | 0.75 |
|   |   |   | CCR5    | 3.97 | 1.171 | 1.12 | 1.145 | 0.93 |
|   |   |   | CD80    | 12.03 | 1.028 | 0.859 | 0.939 | 0.93 |
|   |   |   | CXCL10  | 537.13 | 0.544 | 0.425 | 0.481 | 0.49 |
|   |   |   | CXCL11  | 370.37 | 0.344 | 0.33 | 0.337 | 0.31 |
| S |   |   | CXCL2   | 3.16 | 1.567 | 1.496 | 1.531 | 2.79 |
| S | S | S | CXCL5   | 1.49 | 3.399 | 3.062 | 3.226 | 6.03 |
|   |   |   | CXCL9   | 188.90 | 1.404 | 0.498 | 0.836 | 0.91 |
|   |   | D | DDX58   | 5.81 | 0.719 | 0.704 | 0.711 | 0.94 |
|   |   |   | FOXP3   | 2.73 | 1.117 | 0.906 | 1.006 | 1.11 |
|   |   |   | GATA3   | 0.93 | 1.921 | 2.046 | 1.982 | 2.6 |
|   |   |   | ICAM1   | 3.88 | 1.036 | 0.996 | 1.016 | 0.77 |
|   |   |   | IFNA1   | 10.74 | 1.064 | 1.088 | 1.076 | 1.29 |
| D |   |   | IFNB1   | 4.41 | 0.713 | 0.698 | 0.705 | 0.65 |
| S | S | S | IFNG    | 46.02 | 4.411 | 2.067 | 3.020 | 5.72 |
| S | S | S | IL10    | 3.63 | 2.149 | 1.317 | 1.682 | 3.29 |
|   |   |   | IL12A   | 1.87 | 0.977 | 0.836 | 0.904 | 0.89 |
|   |   | D | IL12B   | 0.73 | 0.969 | 1.556 | 1.228 | 0.23 |
|   |   |   | IL13    | 4.04 | 1.261 | 1.214 | 1.237 | 2.28 |
|   |   |   | IL15    | 3.48 | 1.02 | 0.908 | 0.962 | 0.87 |
|   |   |   | IL16    | 0.68 | 0.958 | 0.891 | 0.924 | 1.02 |
| S | S | S | IL1B    | 3.82 | 9.743 | 5.276 | 7.169 | 21.45 |
|   |   |   | IL1R1   | 0.94 | 0.94 | 1.1 | 1.017 | 1.11 |
|   |   |   | IL1RN   | 18.02 | 0.891 | 0.959 | 0.925 | 0.79 |
|   |   |   | IL2     | 30.96 | 2.21 | 1.68 | 1.927 | 2.48 |
|   |   |   | IL4     | 1.28 | 0.793 | 0.795 | 0.794 | 0.89 |
|   |   | S | IL5     | 1.04 | 0.39 | 0.389 | 0.390 | 0.5 |
| S | S | S | IL8     | 8.76 | 2.607 | 2.56 | 2.583 | 3.86 |
|   |   |   | JAK2    | 4.17 | 0.898 | 0.84 | 0.868 | 0.82 |
|   |   |   | LTA     | 2.77 | 1.043 | 0.797 | 0.911 | 0.99 |
| S | S | S | LYZ     | 0.10 | 0.447 | 0.577 | 0.508 | 0.29 |
| D | D | S | MX1     | 19.39 | 0.641 | 0.591 | 0.616 | 0.66 |
|   |   |   | NOD1    | 1.93 | 0.961 | 0.826 | 0.891 | 0.89 |
| S | S | S | SPP1    | 23.26 | 5.194 | 4.329 | 4.742 | 5.38 |
|   |   |   | STAT1   | 8.26 | 0.936 | 0.725 | 0.824 | 0.91 |
|   |   |   | STAT4   | 1.43 | 1.226 | 0.926 | 1.066 | 1.01 |
|   |   | S | TNF     | 3.09 | 1.568 | 1.351 | 1.456 | 1.2 |
|   |   |   | TNFSF10 | 8.32 | 0.742 | 0.783 | 0.762 | 0.88 |
|   |   |   | TNFSF1313 | 3.42 | 0.903 | 0.948 | 0.926 | 1.07 |

TABLE 11

Comparison of changes in gene expression between groups B/C vs. A day 1, group A day 57 vs. day 1, and groups B/C in stimulus vs. negative control (NC), for heat-killed HSV-1 virus as stimulus.

| Direction of significant change same (S) or different (D) | | | | Heat-killed HSV-1 virus | | | | |
|---|---|---|---|---|---|---|---|---|
| Stimulus v NC and A57 v A1 | Stimulus v NC and B/C v A1 | B/C v A and A57 v A1 | Gene Symbol | fold-stimulation in Virus vs. NC in groups B + C | ratio of absolute gene expression in group vs. group A1 | | | ratio of absolute expression in A57 vs. A1 |
| | | | | | B | C | B + C | |
| S | | | CCL2 | 14.18 | 0.781 | 1.43 | 1.057 | 1.71 |
| S | | | CCL3 | 4.28 | 1.506 | 1.905 | 1.694 | 3.73 |
| S | | | CCL7 | 70.35 | 0.728 | 1.812 | 1.149 | 1.81 |
| | | | CCR5 | 2.14 | 1.022 | 1.227 | 1.119 | 1.35 |
| | | | CD80 | 5.69 | 0.699 | 0.99 | 0.832 | 1.25 |
| | | | CXCL10 | 419.29 | 0.465 | 2.018 | 0.968 | 1 |
| | | | CXCL11 | 88.51 | 0.206 | 0.742 | 0.391 | 0.4 |
| | | | CXCL2 | 2.14 | 0.933 | 0.886 | 0.909 | 1.58 |
| | | | CXCL5 | 0.94 | 1.454 | 1.096 | 1.263 | 2.52 |
| | | | CXCL9 | 111.09 | 1.249 | 2.521 | 1.775 | 2.5 |
| | | | DDX58 | 4.24 | 0.653 | 0.9 | 0.767 | 0.95 |
| S | S | S | FOXP3 | 2.88 | 1.39 | 1.883 | 1.618 | 2.46 |
| S | S | S | GATA3 | 0.57 | 0.45 | 0.361 | 0.403 | 0.32 |
| | | | ICAM1 | 2.50 | 0.96 | 1.262 | 1.100 | 1.07 |
| | | | IFNA1 | 6.35 | 0.607 | 6.193 | 1.938 | 1.34 |
| | | | IFNB1 | 2.45 | 0.86 | 0.961 | 0.909 | 0.87 |
| S | S | S | IFNG | 19.67 | 3.554 | 3.021 | 3.277 | 11.01 |
| | | | IL10 | 1.56 | 0.945 | 0.883 | 0.914 | 2.29 |
| S | S | S | IL12A | 2.26 | 1.154 | 1.429 | 1.284 | 1.48 |
| | | | IL12B | 0.60 | 0.935 | 1.063 | 0.997 | 2.08 |
| S | | | IL13 | 3.88 | 1.44 | 1.6 | 1.518 | 3.02 |
| S | | | IL15 | 3.15 | 1.184 | 1.466 | 1.317 | 1.54 |
| S | S | S | IL16 | 0.69 | 0.83 | 0.737 | 0.782 | 0.82 |
| | | | IL1B | 1.84 | 1.996 | 1.521 | 1.743 | 5.09 |
| | | | IL1R1 | 0.58 | 0.728 | 0.783 | 0.755 | 0.97 |
| | | | IL1RN | 5.41 | 0.995 | 1.265 | 1.122 | 1.48 |
| | | | IL2 | 8.04 | 1.025 | 1.549 | 1.260 | 2.11 |
| | | | IL4 | 1.62 | 1.143 | 1.172 | 1.157 | 1.32 |
| D | D | S | IL5 | 1.39 | 0.504 | 0.63 | 0.563 | 0.56 |
| S | S | S | IL8 | 5.83 | 1.707 | 1.929 | 1.815 | 3.3 |
| | | | JAK2 | 3.52 | 1.038 | 1.377 | 1.195 | 1.26 |
| S | | | LTA | 2.43 | 1.196 | 1.359 | 1.275 | 1.84 |
| | | | LYZ | 0.26 | 0.954 | 0.925 | 0.940 | 0.53 |
| D | D | S | MX1 | 10.06 | 0.374 | 0.835 | 0.559 | 0.66 |
| | | | NOD1 | 1.81 | 0.94 | 1.053 | 0.995 | 1.14 |
| S | S | S | SPP1 | 3.26 | 7.504 | 7.173 | 7.336 | 15.29 |
| | | | STAT1 | 9.34 | 0.953 | 1.367 | 1.141 | 1.41 |
| S | S | S | STAT4 | 1.82 | 1.494 | 1.424 | 1.458 | 1.69 |
| | | | TNF | 2.64 | 0.994 | 1.181 | 1.084 | 1.19 |
| | | | TNFSF10 | 5.92 | 0.659 | 1.155 | 0.873 | 1.01 |
| | | | TNFSF13B | 3.59 | 0.767 | 1.382 | 1.030 | 1.23 |

TABLE 12

Comparison of changes in gene expression between groups B/C vs. A day 1, group A day 57 vs. day 1, and groups B/C in stimulus vs. negative control (NC), with *Candida* extract as stimulus.

| Direction of significant change same (S) or different (D) | | | | *Candida* extract | | | | |
|---|---|---|---|---|---|---|---|---|
| Stimulus v NC and A57 v A1 | Stimulus v NC and B/C v A1 | B/C v A1 and A57 v A1 | Gene Symbol | fold-stimulation in Candida vs. NC in groups B + C | ratio of absolute gene expression in group vs. group A1 | | | ratio of absolute expression in A57 vs. A1 |
| | | | | | B | C | B + C | |
| | | | CCL2 | 2.91 | 0.695 | 0.69 | 0.693 | 1.16 |
| | | | CCL3 | 3.86 | 0.788 | 0.88 | 0.833 | 1.79 |
| S | | | CCL7 | 8.92 | 1.117 | 1.005 | 1.060 | 2.03 |
| | | | CCR5 | 0.73 | 1.484 | 1.055 | 1.251 | 1.42 |
| | | | CD80 | 1.44 | 1.088 | 0.791 | 0.928 | 1.57 |

TABLE 12-continued

Comparison of changes in gene expression between groups B/C vs. A day 1, group A day 57 vs. day 1, and groups B/C in stimulus vs. negative control (NC), with *Candida* extract as stimulus.

| Direction of significant change same (S) or different (D) | | | | *Candida* extract | | | | |
|---|---|---|---|---|---|---|---|---|
| Stimulus v NC and A57 v A1 | Stimulus v NC and B/C v A1 | B/C v A1 and A57 v A1 | Gene Symbol | fold-stimulation in Candida vs. NC in groups B + C | ratio of absolute gene expression in group vs. group A1 | | | ratio of absolute expression in A57 vs. A1 |
| | | | | | B | C | B + C | A1 |
| S | S | S | CXCL10 | 5.94 | 13.595 | 7.96 | 10.403 | 12.8 |
| | | | CXCL11 | 1.93 | 2.839 | 1.381 | 1.980 | 2.53 |
| | | | CXCL2 | 3.72 | 0.568 | 0.802 | 0.675 | 1.1 |
| | | | CXCL5 | 4.57 | 0.601 | 1.074 | 0.803 | 1.45 |
| S | S | S | CXCL9 | 6.95 | 19.598 | 9.046 | 13.315 | 14.21 |
| | | | DDX58 | 1.23 | 1.172 | 1.044 | 1.106 | 1.29 |
| S | S | S | FOXP3 | 2.46 | 1.334 | 1.617 | 1.468 | 2.01 |
| S | S | S | GATA3 | 0.49 | 0.483 | 0.311 | 0.388 | 0.28 |
| | | | ICAM1 | 0.96 | 1.177 | 0.957 | 1.061 | 1.27 |
| | | | IFNA1 | 0.99 | 1.475 | 0.622 | 0.958 | 2.13 |
| | | | IFNB1 | 0.84 | 0.852 | 0.713 | 0.779 | 0.93 |
| S | S | S | IFNG | 9.31 | 4.771 | 2.121 | 3.191 | 8.54 |
| | | | IL10 | 1.44 | 0.655 | 1.109 | 0.852 | 1.12 |
| S | S | S | IL12A | 1.52 | 1.557 | 1.509 | 1.533 | 1.64 |
| S | | | IL12B | 3.38 | 1.343 | 2.436 | 1.809 | 3.61 |
| S | | | IL13 | 5.62 | 1.391 | 2.074 | 1.699 | 4.28 |
| | | S | IL15 | 1.23 | 2.016 | 1.48 | 1.727 | 2.18 |
| S | S | S | IL16 | 0.67 | 0.879 | 0.732 | 0.802 | 0.81 |
| | | | IL1B | 11.21 | 0.473 | 0.687 | 0.570 | 1.73 |
| | | | IL1R1 | 1.01 | 0.618 | 0.898 | 0.745 | 0.9 |
| | | | IL1RN | 1.53 | 1.425 | 1.028 | 1.210 | 1.91 |
| S | | | IL2 | 9.78 | 2.988 | 3.073 | 3.030 | 6.31 |
| S | S | S | IL4 | 1.17 | 1.328 | 1.108 | 1.213 | 1.52 |
| | | | IL5 | 1.08 | 0.916 | 0.773 | 0.842 | 1.1 |
| S | | | IL8 | 6.52 | 0.893 | 1.261 | 1.061 | 1.89 |
| | | S | JAK2 | 1.04 | 1.716 | 1.228 | 1.452 | 1.68 |
| S | | | LTA | 2.10 | 1.238 | 1.514 | 1.369 | 1.94 |
| | | | LYZ | 0.25 | 1.791 | 1.257 | 1.500 | 0.93 |
| | | | MX1 | 0.76 | 0.851 | 0.856 | 0.854 | 1.34 |
| | | | NOD1 | 0.91 | 1.232 | 0.9 | 1.053 | 1.18 |
| | | S | SPP1 | 0.72 | 5.504 | 3.638 | 4.475 | 7.34 |
| S | S | S | STAT1 | 2.27 | 2.518 | 2.044 | 2.269 | 3.36 |
| S | S | S | STAT4 | 1.35 | 1.766 | 1.47 | 1.611 | 1.76 |
| | | | TNF | 1.76 | 1.02 | 1.036 | 1.028 | 1.22 |
| | | | TNFSF10 | 1.12 | 1.306 | 1.143 | 1.222 | 1.52 |
| | | | TNFSF13B | 0.70 | 1.285 | 1.19 | 1.237 | 1.62 |

TABLE 13

Comparison of changes in gene expression between groups B/C vs. A day 1 and group A day 57 vs. day 1 in negative control (NC) medium (unstimulated condition).

| Direction of significant change same (S) or different (D) | | | | Negative control | | | | |
|---|---|---|---|---|---|---|---|---|
| Stimulus v NC and A57 v A1 | Stimulus v NC and B/C v A1 | B/C v A1 and A57 v A1 | Gene Symbol | fold-stimulation in stimulus vs. NC in groups B + C | ratio of absolute gene expression in group vs. group A1 | | | ratio of absolute expression in A57 vs. A1 |
| | | | | | B | C | B + C | A1 |
| Not applicable | Not applicable | | CCL2 | Not applicable | 0.437 | 0.627 | 0.523 | 1.15 |
| | | | CCL3 | | 0.875 | 0.829 | 0.851 | 1.79 |
| | | | CCL7 | | 0.461 | 0.462 | 0.462 | 1.35 |
| | | | CCR5 | | 1.351 | 1.484 | 1.416 | 1.19 |
| | | | CD80 | | 0.949 | 1.04 | 0.994 | 1.16 |
| | | | CXCL10 | | 2.374 | 3.626 | 2.934 | 0.68 |
| | | | CXCL11 | | 6.159 | 2.192 | 3.675 | 0.83 |
| | | | CXCL2 | | 0.444 | 0.484 | 0.464 | 1.33 |
| | | | CXCL5 | | 0.467 | 0.353 | 0.406 | 1.78 |
| | | | CXCL9 | | 6.281 | 30.263 | 13.788 | 4.93 |

TABLE 13-continued

Comparison of changes in gene expression between groups B/C vs. A day 1 and group A day 57 vs. day 1 in negative control (NC) medium (unstimulated condition).

| Direction of significant change same (S) or different (D) | | | | Negative control | | | | |
|---|---|---|---|---|---|---|---|---|
| Stimulus v NC and A57 v A1 | Stimulus v NC and B/C v A1 | B/C v A1 and A57 v A1 | Gene Symbol | fold-stimulation in stimulus vs. NC in groups B + C | ratio of absolute gene expression in group vs. group A1 | | | ratio of absolute expression in A57 vs. A1 |
| | | | | | B | C | B + C | |
| | | S | DDX58 | 0.805 | 1.064 | 0.926 | 0.83 | |
| | | | FOXP3 | 0.87 | 1.289 | 1.059 | 1.07 | |
| | | | GATA3 | 0.749 | 0.785 | 0.767 | 0.84 | |
| | | | ICAM1 | 1.255 | 1.429 | 1.339 | 1.34 | |
| | | | IFNA1 | 0.527 | 0.7 | 0.607 | 1.47 | |
| | | | IFNB1 | 0.737 | 0.923 | 0.825 | 0.73 | |
| | | | IFNG | 0.885 | 1.235 | 1.045 | 1.24 | |
| | | | IL10 | 0.706 | 1.11 | 0.885 | 1.04 | |
| | | | IL12A | 0.989 | 1.169 | 1.075 | 0.98 | |
| | | | IL12B | 0.563 | 0.982 | 0.743 | 1.38 | |
| | | | IL13 | 1.307 | 1.751 | 1.513 | 1.69 | |
| | | | IL15 | 1.22 | 1.247 | 1.233 | 1.13 | |
| | | | IL16 | 0.938 | 0.969 | 0.954 | 0.89 | |
| | | | IL1B | 0.403 | 0.284 | 0.338 | 2.09 | |
| | | S | IL1R1 | 0.516 | 0.745 | 0.620 | 0.6 | |
| | | | IL1RN | 1.515 | 1.074 | 1.276 | 1.35 | |
| | | | IL2 | 0.803 | 1.444 | 1.077 | 1.21 | |
| | | | IL4 | 1.04 | 0.955 | 0.997 | 0.98 | |
| | | S | IL5 | 0.404 | 0.642 | 0.510 | 0.39 | |
| | | | IL8 | 1.018 | 0.954 | 0.986 | 2.38 | |
| | | | JAK2 | 1.096 | 1.208 | 1.151 | 0.93 | |
| | | | LTA | 0.767 | 0.834 | 0.800 | 0.73 | |
| | | | LYZ | 1.199 | 1.023 | 1.107 | 0.55 | |
| | | S | MX1 | 0.657 | 1.028 | 0.822 | 0.47 | |
| | | | NOD1 | 0.988 | 1.07 | 1.028 | 0.87 | |
| | | | SPP1 | 5.356 | 4.246 | 4.769 | 2.38 | |
| | | | STAT1 | 1.592 | 1.728 | 1.659 | 1.29 | |
| | | | STAT4 | 1.02 | 0.988 | 1.004 | 0.88 | |
| | | | TNF | 1.018 | 1.202 | 1.106 | 1.15 | |
| | | | TNFSF10 | 0.957 | 1.449 | 1.178 | 1 | |
| | | | TNFSF13B | 0.793 | 1.255 | 0.998 | 0.67 | |

IFNG was significantly more expressed in groups B+C combined than group A day 1 in all three stimuli. The other genes besides IFNG significantly more expressed in groups B+C than A in HSV1-infected cell extracts were CCL3, CCL5, DDX58, IL1B, IL8, and SPP1. In HSV-1 virions they were FOXP3 and SPP1; and in *Candida* extract they were CXCL10, FOXP3, SPP1, STAT1, and STAT4. The genes significantly less expressed in groups B+C than A in HSV-1 infected cell extracts were IL5, LYZ, and MX1; in HSV-1 virions the genes less expressed in groups B+C than A were GATA3, IL16, and IL5; and in *Candida* extract they were GATA3 and IL16.

Every one of those genes with increased expression in groups B+C vs. A was an upregulated gene in the stimulus and every gene with decreased expression in groups B+C vs. A was a downregulated gene in the stimulus, except DDX58 in HSV-1 infected cell extracts was less expressed in B+C but upregulated, and IL5 was less expressed in B+C vs. A in HSV-1-infected cell extracts and HSV-1 virus, but upregulated very modestly in the virus, and SPP1 was more expressed in B+C vs. A in *Candida* but neither significantly nor upregulated nor downregulated in *Candida*.

Many genes had significant changes in gene expression in group A on day 57 compared to day 1 in the three stimuli, and in essentially every case the same gene's expression was also changed in in the same direction in groups B+C compared to A1. In fact, for every gene with a significant change in A57 vs. A1 and in group B+C combined vs. A1 the change was in the same direction. These were the following: In HSV-1-infected cell extracts, CCL3, CCL5, IFNG, IL10, IL1B, IL8 and SPP1 were increased, and IL5, IL12B, LYZ, and MX1 were decreased. In heat-killed HSV-1 virus, FOXP3, IFNG, IL12A, IL8, SPP1, and STAT4 were increased, and IL5, GATA3, IL16, and MX1 were decreased. In *Candida* extract, CXCL10, FOXP3, IFNG, IL12A, SPP1, STAT1, and STAT4 were increased, and GATA3 and IL16 were decreased.

In the unstimulated negative control condition the only genes with a significant difference in gene expression in both (groups B, C, or B+C vs. group A day 1) and (group A day 57 vs. day 1) were DDX58, IL1R1, IL5, and MX1, and each of those genes was less expressed in groups B/C than in A and in group A day 57 than on day 1 in the unstimulated negative control condition. So here also, all four changes in gene expression were in the same direction to make group A on day 57 more like those with better immune control of the HSV-1.

Changes in gene expression in group A from day 1 to days 15 and 57.

The ratios of day 15/day 1 and day 57/day 1 PBMC absolute gene expression in group A are shown in Table 14. In the three stimulated conditions, there were far more significant differences in gene expression on day 57 than on day 15 compared to day 1, and that is why the day 57 data only is used in Tables 10-13. This is consistent with the PBMC proliferation data that shows essentially no change in proliferation at day 15 but an increase in proliferation in all three stimuli on day 57. But interestingly in the negative control condition there are several genes that are significantly less expressed on day 15 than day 1 and are not at day 57, specifically CCL2, CCL7, CD80, CXCL2, CXCL5, IL12B, and IL1B.

TABLE 14

Ratios of PBMC absolute gene expression in group A on days 15 and 57 compared to day 1.

| | Group A day 15/day 1 | | | | | Group A day 57/day 1 | | | |
|---|---|---|---|---|---|---|---|---|---|
| Gene | Neg. control | HSV-infected cell extracts | Virus | Candida | Gene | Neg. control | HSV-infected cell extracts | Virus | Candida |
| CCL2 | 0.35 | 0.88 | 0.88 | 0.73 | CCL2 | 1.15 | 1.21 | 1.71 | 1.16 |
| CCL3 | 0.47 | 1.31 | 0.84 | 0.33 | CCL3 | 1.79 | 4.60 | 3.73 | 1.79 |
| CCL7 | 0.25 | 0.92 | 0.72 | 0.66 | CCL7 | 1.35 | 0.75 | 1.81 | 2.03 |
| CCR5 | 1.00 | 1.00 | 0.87 | 1.16 | CCR5 | 1.19 | 0.93 | 1.35 | 1.42 |
| CD80 | 0.66 | 0.90 | 0.79 | 0.75 | CD80 | 1.16 | 0.93 | 1.25 | 1.57 |
| CXCL10 | 0.94 | 0.82 | 0.74 | 2.87 | CXCL10 | 0.68 | 0.49 | 1.00 | 12.8 |
| CXCL11 | 0.62 | 0.53 | 0.34 | 1.06 | CXCL11 | 0.83 | 0.31 | 0.40 | 2.53 |
| CXCL2 | 0.51 | 1.02 | 0.91 | 0.39 | CXCL2 | 1.33 | 2.79 | 1.58 | 1.10 |
| CXCL5 | 0.36 | 1.24 | 0.94 | 0.46 | CXCL5 | 1.78 | 6.03 | 2.52 | 1.45 |
| CXCL9 | 2.50 | 1.12 | 1.42 | 2.52 | CXCL9 | 4.93 | 0.91 | 2.5 | 14.21 |
| DDX58 | 0.82 | 0.72 | 0.66 | 1.08 | DDX58 | 0.83 | 0.94 | 0.95 | 1.29 |
| FOXP3 | 0.95 | 1.15 | 1.27 | 1.16 | FOXP3 | 1.07 | 1.11 | 2.46 | 2.01 |
| GATA3 | 1.06 | 2.84 | 0.89 | 1.12 | GATA3 | 0.84 | 2.6 | 0.32 | 0.28 |
| ICAM1 | 1.10 | 1.05 | 1.01 | 1.03 | ICAM1 | 1.34 | 0.77 | 1.07 | 1.27 |
| IFNA1 | 1.20 | 0.80 | 0.58 | 1.42 | IFNA1 | 1.47 | 1.29 | 1.34 | 2.13 |
| IFNB1 | 0.99 | 0.65 | 0.78 | 1.03 | IFNB1 | 0.73 | 0.65 | 0.87 | 0.93 |
| IFNG | 1.05 | 1.26 | 1.91 | 0.81 | IFNG | 1.24 | 5.72 | 11.01 | 8.54 |
| IL10 | 0.90 | 1.19 | 0.74 | 0.6 | IL10 | 1.04 | 3.29 | 2.29 | 1.12 |
| IL12A | 0.84 | 0.90 | 0.94 | 1.02 | IL12A | 0.98 | 0.89 | 1.48 | 1.64 |
| IL12B | 0.40 | 0.80 | 0.59 | 0.78 | IL12B | 1.38 | 0.23 | 2.08 | 3.61 |
| IL13 | 0.88 | 1.01 | 1.43 | 0.6 | IL13 | 1.69 | 2.28 | 3.02 | 4.28 |
| IL15 | 0.95 | 0.93 | 1.01 | 1.09 | IL15 | 1.13 | 0.87 | 1.54 | 2.18 |
| IL16 | 1.06 | 1.03 | 0.84 | 1.02 | IL16 | 0.89 | 1.02 | 0.82 | 0.81 |
| IL1B | 0.16 | 1.48 | 0.77 | 0.17 | IL1B | 2.09 | 21.45 | 5.09 | 1.73 |
| IL1R1 | 1.00 | 0.89 | 0.74 | 0.69 | IL1RI | 0.6 | 1.11 | 0.97 | 0.9 |
| IL1RN | 0.90 | 0.94 | 0.77 | 1 | IL1RN | 1.35 | 0.79 | 1.48 | 1.91 |
| IL2 | 0.80 | 0.98 | 1.43 | 0.75 | IL2 | 1.21 | 2.48 | 2.11 | 6.31 |
| IL4 | 0.86 | 0.77 | 0.80 | 1.12 | IL4 | 0.98 | 0.89 | 1.32 | 1.52 |
| IL5 | 0.99 | 0.83 | 0.76 | 1.23 | IL5 | 0.39 | 0.50 | 0.56 | 1.10 |
| IL8 | 0.62 | 0.99 | 1.13 | 0.44 | IL8 | 2.38 | 3.86 | 3.3 | 1.89 |
| JAK2 | 0.91 | 0.86 | 0.84 | 1.1 | JAK2 | 0.93 | 0.82 | 1.26 | 1.68 |
| LTA | 0.94 | 1.03 | 1.26 | 1.15 | LTA | 0.73 | 0.99 | 1.84 | 1.94 |
| LYZ | 1.18 | 0.73 | 1.04 | 2.22 | LYZ | 0.55 | 0.29 | 0.53 | 0.93 |
| MX1 | 0.81 | 0.89 | 0.49 | 1.28 | MX1 | 0.47 | 0.66 | 0.66 | 1.34 |
| NOD1 | 1.14 | 1.04 | 0.85 | 1.19 | NOD1 | 0.87 | 0.89 | 1.14 | 1.18 |
| SPP1 | 1.35 | 2.09 | 1.64 | 2.32 | SPP1 | 2.38 | 5.38 | 15.29 | 7.34 |
| STAT1 | 0.86 | 0.90 | 0.80 | 1.12 | STAT1 | 1.29 | 0.91 | 1.41 | 3.36 |
| STAT4 | 0.94 | 0.89 | 1.03 | 1.07 | STAT4 | 0.88 | 1.01 | 1.69 | 1.76 |
| TNF | 0.91 | 1.17 | 0.97 | 0.85 | TNF | 1.15 | 1.2 | 1.19 | 1.22 |
| TNFSF10 | 0.93 | 0.84 | 0.68 | 1.02 | TNFSF10 | 1.00 | 0.88 | 1.01 | 1.52 |
| TNFSF13B | 1.03 | 0.93 | 0.77 | 1.14 | TNFSF13B | 0.67 | 1.07 | 1.23 | 1.62 |

Group a Goes from Lower IFNG Expression than Groups B+C on Day 1 to Higher than Groups B+C on Day 57 in all Three Stimuli.

Table 15 shows how the expression of the IFNG gene in group A on days 1 and 57 compares to groups B+C pooled. At day 1, group A's expression of IFNG was significantly less than groups B+C pooled in all three stimuli. At day 57, it was above that of groups B+C in all three stimuli, and was significantly more than groups B+C in heat-killed HSV virus. So with the HSV-1 virus stimulus, expression of IFNG in the frequent herpes labialis sufferers goes from significantly less than groups B+C to significantly more than them 56 days after treatment with SADBE. Thus, SADBE treatment does not just partially reduce the defect in IFNG expression in those with frequent herpes labialis episodes, it completely reverses it.

TABLE 15

Ratio of expression of the IFNG gene in group A on days 1 and 57 vs. Groups B + C pooled.

| | Ratio of absolute IFNG gene expression in group A vs. Groups B + C pooled | | | |
|---|---|---|---|---|
| | Neg Control | HSV-infected cell extracts | Virus | Candida |
| Group A, day 1 | 0.957 | 0.331* | 0.305* | 0.314* |
| Group A day 57 | 1.190 | 1.896 | 3.359* | 2.684 |

*Statistically significant difference vs. B + C pooled, p < 0.05

Discussion

The data here shows a cellular immune response is more important than humoral and a Th1 immune response more important than Th2 in controlling HSV-1 outbreaks as herpes labialis. And it shows that a single dose of SADBE changes the immune response of subjects with frequent herpes labialis over 8 weeks to make it more like, and in some key respects better than, the immune response of subjects with few or no herpes labialis outbreaks.

PBMC Proliferation In Vitro to HSV-1 and Other Stimuli.

PBMC proliferation in response to all three stimuli showed the same trends of group C>B>A. In other words, PBMC from those with better immune control of HSV-1 proliferated more than those with worse immune control. The difference was not statistically significant for any one stimulus, but the response to all three stimuli taken together was significantly greater in group C than group A (when the highest and lowest proliferation data point outliers from each group of 12 subjects were removed).

PBMC proliferation against HSV-1 of the group A subjects was significantly greater on day 57 than on day 1 before drug treatment. The PBMC proliferative response to all three stimuli taken together was also significantly greater on day 57 than day 1 in the group A subjects when the highest and lowest proliferation data point outliers were removed from the analysis. Thus, the group A subjects were more like the group C subjects with good immune control of HSV infection 56 days after SADBE treatment than they had been on day 1 before drug treatment.

Anti-HSV-1 IgG

Groups C and B pooled together had significantly lower anti-HSV-1 IgG levels than group A. Among group A subjects, anti-HSV-1 IgG levels were lower on day 57 than day 1, although not significantly so, making the group A subjects again more like those with fewer outbreaks and better immune control of the virus on day 57 than they had been on day 1.

Immune Gene Expression

For almost every immune-related gene where any differences were significant the direction of these changes match:
1. Expression in PBMCs upregulated (or downregulated) by HSV-1 (or other stimulus).
2. Same upregulated gene was more expressed in the presence of HSV-1 (or other stimulus) in group C and B subjects (those with zero or infrequent herpes labialis episodes) than group A subjects (those with frequent herpes labialis episodes). (If the gene was downregulated by the stimulus, then it was also found to be less expressed in groups C and B than group A.)
3. Same upregulated gene was more expressed in the presence of HSV-1 (or other stimulus) in group A subjects on day 57 after treatment with SADBE than on day 1 before treatment. (If the gene was downregulated by the stimulus, then it was also found to be less expressed in group A on day 57 than day 1.)

Thus in essentially every case, the SADBE treatment changed the group A subjects by day 57 to make them much more like the group B and C subjects who have better immune control of their HSV-1 infection than the group A subjects were on day 1.

IFNG (a Th1 cytokine) was the gene (1) most consistently upregulated by a large amount in all three stimuli versus negative control, (2) most consistently increased by the greatest amount in its expression in groups B+C versus group A day 1 in all three stimuli, and (3) most consistently increased in its expression by the greatest amount in group A day 57 vs. day 1 in all three stimuli. IL5 (a Th2 cytokine) (1) was not upregulated by any of the three stimuli and (2) was less expressed in groups B+C than group A day 1 in both HSV-1 virus and HSV-1-infected cell extracts, and (3) was less expressed in group A on day 57 than day 1 in both HSV-1 virus and HSV-1-infected cell extracts.

The data indicate that cell-mediated immunity is more important than humoral immunity and a type 1 cell-mediated response more important than a type-2 response in control of HSV-1 infection and indicate that PBMC proliferation in vitro in response to the HSV-1 virus correlates with effective immune control. Interferon gamma (IFNG) was found to be perhaps the gene whose expression in PBMCs is most correlated with effective immune control of HSV-1.

SADBE treatment not only decreased the gap in immune performance of the subjects with frequent outbreaks relative to the healthier groups, it completely eliminated and even reversed the gap in key measures. On day 57 the group A subjects were actually outperforming the subjects with fewer or zero outbreaks on the key immune measures of PBMC proliferative response to virus and IFNG gene expression in response to virus.

These results are consistent with, and tend to confirm, the results of the prior clinical trial that showed a single topical application of 2% SADBE to the arm delayed next cold sore outbreak in persons with frequent cold sores (Palli 2017). Interestingly, in the clinical trial there was a suggestion in the data that SADBE did not exert its effect until more than about 3 weeks after drug application, and in this study also the increase in PBMC response to HSV-1 after SADBE application in both PBMC proliferation and immune gene expression was greater at 8 weeks after drug application than at 2 weeks after drug application.

Others have previously shown that CD8+ T cells were important in controlling herpes labialis outbreaks (Cunningham 1985, Koelle 1994, Koelle 2001, Koelle 1998, Liu 2000, Dobbs 2005, Sheridan 2009, Hoshino 2007, Liu 2000, Egan 2013). Our data is consistent with this. The helper/cytotoxic cell ratio (CD4+/CD8+ ratio) which was 5.25 in group A vs. 3.07 and 3.15 respectively in groups B and C. The p value is less than 0.20 for comparisons of group A to both groups B and C, and if groups B and C are pooled and compared to group A the p value is 0.065, almost significant. This is consistent with prior evidence discussed below that CD8+ T cells are important and effective in controlling HSV recurrences.

Consistent with our finding lower anti-HSV-1 IgG levels correlate with better control of HSV-1 outbreaks, Spruance (1995) also found lower serum anti-HSV-1 antibodies in HSV seropositive patients with a history of frequent herpes labialis than in seropositive persons with no history of herpes labialis.

Several prior reports also found IFN-gamma to be important in controlling HSV infection and reducing HSV outbreaks. Dobbs (2005) showed that CD8+ T cells were able to clear an HSV-2 infection in transgenic mice, but that efficacy was blocked in vivo by anti-IFNG IgG. Liu (2001) showed that CD8+ T-cells could prevent HSV-1 reactivation from latency in excised trigeminal ganglia (TG), and that IFN-gamma protein was produced by the CD8+ T cells, and that neutralization of IFN-γ significantly enhanced the rate of HSV-1 reactivation from latency in TG cultures (Liu 2001). Spruance (1995) found that IFN-gamma protein levels in PBMC supernatants stimulated with HSV-1-infected cell extracts were lower in frequent herpes labialis sufferers than HSV-1 seropositive controls, consistent with the present result for IFNG gene expression in PBMC stimulated with heat-killed HSV-1. Cunningham (1983) showed higher interferon levels (including alpha, gamma, and lambda) in supernatants of PBMCs stimulated with heat-killed HSV-1 virus correlated with longer time to next herpes labialis recurrence. Carr (2009) showed that transgenic expression of IFNG could prevent HSV-1 reactivation in a mouse model.

Our data is consistent with this in linking IFNG expression with frequency of herpes labialis outbreaks. IFNG the key Th1 cytokine, was at least 9-fold overexpressed in groups B+C in the stimuli vs. negative control, at least 3-fold more highly expressed in all three stimuli in groups B+C than group A on day 1, and at least 8-fold more expressed in all three stimuli in group A on day 57 than day 1.

Conversely, IL5, a Th2 cytokine, was not upregulated significantly in groups B+C in any of the three stimuli vs. negative control, was significantly less expressed in groups B+C than group A on day 1 in both HSV-infected cell extracts and heat-killed HSV-1 virus, and in the negative control condition, and was significantly less expressed in both HSV-infected cell extracts and HSV1-virus and in the negative control in group A on day 57 than on day 1. IL-5 stimulates B cells and antibody production (Takatsu 1998, Spellberg 2001), so the fact that its expression in the HSV-1-stimulated PBMCs is positively correlated with frequent recurrences is further evidence that antibody production is not important for control of recurrences.

Thus, the two genes that appear to be most linked to immune prevention of HSV-1 outbreaks but in opposite directions are IFNG (increased expression in both HSV stimuli) and IL5 (decreased expression in both HSV stimuli). This link of lower IL5 expression or protein level to reduced HSV-1 recurrences has not previously been shown to our knowledge.

SADBE appears to somehow reset the immune system 8 weeks after drug application to more of a type 1 cellular immune response and a larger cellular immune response to the virus—with greater PBMC proliferation against heat-killed HSV-1, and greater IFNG expression and lower IL5 expression in response to both the heat-killed HSV-1 virus and HSV-1-infected cell extracts. These same differences characterize HSV-1-seropositive subjects with few or no herpes labialis outbreaks as opposed to those with frequent outbreaks, so SADBE resets the immune response to the virus to more like that of persons with more effective immune control of the virus.

Moreover, SADBE dosing did not just ameliorate the defect in group A immune response to HSV-1, it completely reversed it in the key measures of PBMC proliferation in response to heat-inactivated HSV-1 virus and IFNG expression in the presence of HSV-1 virus: At day 1 group A had lower proliferation than groups B and C in the presence of HSV-1 virus and significantly lower IFNG expression than groups B+C, whereas at day 57 group A had higher PBMC proliferation than groups B and C in the presence of HSV-1 virus and significantly higher IFNG expression than groups B+C.

Interestingly, those with fewer or no herpes labialis outbreaks also mounted a larger immune response to *Candida* extract, even though it is unrelated to herpes—with greater PBMC proliferation to *Candida* extract and greater expression of upregulated immune genes in *Candida* extract, including IFNG, and lower expression of down-regulated immune genes in *Candida* extract. And interestingly, SADBE application also improved the immune response to the *Candida* extract in the same ways in subjects with frequent herpes labialis outbreaks 8 weeks after SADBE application. This suggests SADBE application on the arm would also be effective to improve immune response to yeast infection anywhere in the body.

References

Annunziato F, Romagnani C, Romagnani S. 2015. The 3 major types of innate and adaptive cell-mediated effector immunity. *J Allergy Clin Immunol.* 135:626-35.

Carr D J, Austin B A, Halford W P, Stuart P M. 2009. Delivery of Interferon-gamma by an adenovirus vector blocks herpes simplex virus Type 1 reactivation in vitro and in vivo independent of RNase L and double-stranded RNA-dependent protein kinase pathways. *J Neuroimmunol.* 206(1-2):39-43.

Corbera-Bellalta M, Planas-Rigol E, Lozano E, Terrades-Garcia N, Alba M A, Prieto-Gonzalez S, Garcia-Martinez A, Albero R, Enjuanes A, Espígol-Frigolé G, Hernández-Rodríguez J, Roux-Lombard P, Ferlin W G, Dayer J M, Kosco-Vilbois M H, Cid M C. 2016. Blocking interferon γ reduces expression of chemokines CXCL9, CXCL10 and CXCL11 and decreases macrophage infiltration in ex vivo cultured arteries from patients with giant cell arteritis. *Ann Rheum Dis.* 75(6):1177-86.

Cunningham A L and Merigan T C 1983 Gamma interferon production appears to predict time of recurrence of herpes labialis. J. immunol. 130:2397-2400.

Cunningham, A. L., R. R. Turner, A. C. Miller, M. F. Para, and T. C. Merigan. 1985. Evolution of recurrent herpes simplex lesions: an immunohistologic study. *J. Clin. Invest.* 75:226-233.

Daheshia M, Feldman L T, Rouse B T. 1998. Herpes simplex virus latency and the immune response. *Curr. Opin. Microbiol.* 1:430-436.

Dobbs, M E, Jane E. Strasser, Chin-Fun Chu, Claudia Chalk, Gregg N. Milligan. 2005. Clearance of Herpes Simplex Virus Type 2 by CD8+ T Cells Requires Gamma Interferon and either Perforin- or Fas-Mediated Cytolytic Mechanisms. *J Virol.* 79(23): 14546-14554.

Egan K P, Wu S, Wigdahl B, Jennnings S R. 2013 Immunological control of herpes simplex virus infections. J. Neurovirol. 19:328-345

Haller O, Staeheli P, Kochs G. 2007. Interferon-induced Mx proteins in antiviral host defense. *Biochimie.* 89(6-7):812-8.

Hoshino Y, Pesnicak L, Cohen J I, Straus S E. 2007. Rates of reactivation of latent herpes simplex virus from mouse trigeminal ganglia ex vivo correlate directly with viral load and inversely with number of infiltrating CD8+ T cells. *J Virol.* 81(15):8157-64.

Kim C H. 2009. FOXP3 and its role in the immune system. *Adv Exp Med Biol.* 665:17-29.

Koelle, D. M., H. Abbo, A. Peck, K. Ziegweid, and L. Corey. 1994. Direct recovery of herpes simplex virus (HSV)- specific T lymphocyte clones from recurrent genital HSV-2 lesions. *J. Infect. Dis.* 169:956-961.

Koelle, D. M., C. M. Posavad, G. R. Barnum, M. L. Johnson, J. M. Frank, and L. Corey. 1998. Clearance of HSV-2 from recurrent genital lesions correlates with infiltration of HSV-specific cytotoxic T lymphocytes. *J. Clin. Invest.* 101:1500-1508.

Koelle, D. M., H. Chen, M. A. Gavin, A. Wald, W. W. Kwok, and L. Corey. 2001. CD8 CTL from genital herpes simplex lesions: recognition of viral tegument and immediate early proteins and lysis of infected cutaneous cells. *J. Immunol.* 166:4049-4058.

Lee A N, Mallory S B. 1999. Contact immunotherapy with squaric acid dibutylester for the treatment of recalcitrant warts. *J Am Acad Dermatol.* 41(4):595-599.

Liu T, Khanna K M, Chen X, Fink D J, Hendricks R L. 2000. CD8(+) T cells can block herpes simplex virus type 1 (HSV-1) reactivation from latency in sensory neurons. *J Exp Med.* 191(9):1459-66.

Liu T, Khanna K M, Carriere B N, Hendricks R L. 2001. Gamma interferon can prevent herpes simplex virus type 1 reactivation from latency in sensory neurons. *J Virol.* 75: 11178-11184.

Lorette G, Crochard A, Mimaud V, Wolkenstein P, Stalder J F, El Hasnaoui A. 2006. A survey on the prevalence of orofacial herpes in France: the INSTANT Study. *J Am Acad Dermatol.* 55(2):225-232.

McKennaDB, Neill W A, Norval M. 2001. Herpes simplex virus-specific immune responses in subjects with frequent and infrequent orofacial recrudescences. *British J. Dermatology* 144:459-464.

Minton K. 2017. Haematopoiesis: Osteopontin skews lymphoid-myeloid balance. *Nat Rev Immunol.* 17(8):466-467.

Nicoll, M P; Proenca, J T, and Efstathiou, S. 2012. The molecular basis of herpes simplex virus latency. *FEMS Microbiol Rev.* 36:684-705.

Opstelten W, Neven A K, Eekhof J. Treatment and prevention of herpes labialis. 2008. *Can Fam Physician.* 54(12): 1683-1687.

Palli M A, McTavish H, Kimball A, Horn T D. 2017 Immunotherapy of Recurrent Herpes Labialis With Squaric Acid. *JAMA Dermatol.* 153:828-829

Park H J, Choi Y W, Kim S H, Shin M S, Lee S W, Oh M K, Choi H Y. 2013. Change in cytokines in patients with warts after contact immunotherapy with squaric acid dibutyl ester. *Clinical and Experimental Dermatology* 38:775-781.

Parks C G, Andrew M E, Blanciforti L A, Luster M I. 2007. Variation in the WBC differential count and other factors associated with reporting of herpes labialis: a population-based study of adults. *FEMS Immunol Med Microbiol.* 51(2):336-343.

Rokhsar C K, Shupack J L, Vafai J J, Washenik K. 1998. Efficacy of topical sensitizers in the treatment of alopecia areata. *J Am Acad Dermatol.* 39(5 Pt 1):751-761.

Sarnoff D S. Treatment of recurrent herpes labialis. 2014. *J Drugs Dermatol.* 13(9):1016-1018.

Sheridan B S, Cherpes T L, Urban J, Kalinski P, Hendricks. 2009. Reevaluating the CD8 T-cell response to herpes simplex virus type 1: involvement of CD8 T cells reactive to subdominant epitopes. *J. Virol.* 83:2237-2245.

Silverberg N B, Lim J K, Paller A S, Mancini A J. 2000. Squaric acid immunotherapy for warts in children. *J Am Acad Dermatol.* 42(5 Pt 1):803-808.

Spellberg B, Edwards J E Jr. 2001. Type 1/Type 2 immunity in infectious diseases. *Clin Infect Dis.* 32(1):76-102.

Spruance S L, Evans T G, McKeough M B, Thai L, Araneo B A, Daynes R A, Mishkin E M, Abramovitz A S. 1995. Th1/Th2-like immunity and resistance to herpes simplex labialis. *Antiviral Res.* 28(1):39-55.

Takatsu K. Interleukin 5 and B cell differentiation. 1998. *Cytokine Growth Factor Rev.* 9(1):25-35.

Wan Y Y. 2014. GATA3: a master of many trades in immune regulation. *Trends Immunol.* 35(6):233-42.

Woo S B, Challacombe S J. 2007. Management of recurrent oral herpes simplex infections. *Oral Surg Oral Med Oral Pathol Oral Radiol Endod.* 103 Suppl:S12.e11-18.

Zhu J, Yamane H, Cote-Sierra J, Guo L, Paul W E. 2006. GATA-3 promotes Th2 responses through three different mechanisms: induction of Th2 cytokine production, selective growth of Th2 cells and inhibition of Th1 cell-specific factors. *Cell Res.* 16(1):3-10.

EXAMPLE 2

Treatment of Herpes Labialis by Squaric Acid Dibutyl Ester

Thirty patients are recruited meeting the following criteria:

| Inclusion Criteria | Exclusion Criteria |
| --- | --- |
| 18-85 years old | |
| Men and non-pregnant/non-lactating women | Pregnancy or attempting to become pregnant |
| Able to understand and comply with all requirements of protocol | Unable to return for follow-up visits or comply with protocol |
| Six or more episodes of herpes labialis of a recurring nature per year | Prior treatment with Squaric Acid and current active therapy |
| | Cancer treatment and any immunodeficiency |

In a screening interview, vital signs are recorded, and information is collected on any medications the patient is currently taking, previous and current treatments for cold sores, severity and duration of cold sores.

Visit 1: Upon entering the study, patients are sensitized to squaric acid dibutyl ester (SADBE) by dipping a cotton-tipped swab in a 2% solution of SADBE in DMSO and swabbing a 1 cm$^2$ area on the forearm. Participants are told then to wait at least 2 weeks for their first treatment.

Throughout the study, the participants are asked to maintain a subject diary, in which they record each day any symptoms they experience, including fever, swelling, pain, redness, itching, burning, the size of any lesions, and any medications taken.

Visit 2: After the 2-week period to allow development of sensitivity to SADBE, upon the beginning of his or her next outbreak (within 72 hours of the first signs of an outbreak), each participant is swabbed at the site of the herpes labialis lesion with a 0.5% solution of SADBE in DMSO.

Visit 3: Upon the next distinct outbreak at least 2 weeks after the previous treatment at visit 2, study diaries are collected. If the diary reflects redness, blistering, or burning greater than 0.5 cm beyond the clinical lesion with the previous SADBE treatment, the dosage of SADBE is decreased to 0.1%. If the diary reflects no redness or inflammation attributable to SADBE treatment, dosage is increased to 2%. Otherwise, dosage is maintained at 0.5%. Participants are swabbed at the site of the herpes labialis lesion with the SADBE solution.

If the hypersensitivity reaction produced by SADBE is excessive, patients are treated with a topical steroidal anti-inflammatory cream. When a patient requests, outbreaks are treated with oral valacyclovir until the outbreak resolves.

For at least 6 months after visit 2, patients maintain their diaries. Every two months the diaries are collected.

At visit 1, before applying SADBE, a blood sample is collected from each patient for use in a peripheral blood mononuclear cell (PBMC) proliferation assay to test immune response to herpes virus.

Two months after visit 2 (the first treatment application of SADBE to an HSV lesion) if the patient has not experienced a recurrence outbreak after visit 2, or one month after visit 3 (the treatment application of SADBE to a lesion of a second outbreak), a blood sample is collected from the patient. The first, pretreatment, blood sample and the second, posttreatment, blood sample are used to conduct PBMC proliferation assays to test immune response to herpes virus before and after treatment.

PBMC Proliferation Assay

Venous blood is collected in heparinized test tubes for mononuclear cell isolation prior to treatment and after treatment at the times described above. Sample specimens are immediately transferred to the laboratory for processing.

Venous blood (15 ml) is transferred to a 50 ml centrifuge tube, diluted to a total volume of 30 ml with saline or PBS, underlayed with Fico/Lite-LymphoH™ (Atlanta Biologicals) and centrifuged for 20 minutes at 2100 rpm in an Eppendorf Model 5804R centrifuge. Interface cells are collected and washed 2× with saline/PBS, centrifuged and resuspended in saline/PBS. Cell counts are performed using a Beckman Coulter Z1 particle counter and the cells resuspended in freezing media (RPMI/20% human AB serum) and stored at −70° C. Pre- and post-treatment peripheral blood mononuclear cells from each patient are stored for proliferation assays.

KOS HSV-1 virus (American Type Culture Collection) is grown in culture in VERO cells and collected. Virus is filtered through a 45:m filter attached to a 3 ml syringe, into sterile cryovials. The titer of the virus stock is determined. Virus is then heat inactivated, and stored at −20° C. for use to stimulate PMBC in the proliferation assays.

Peripheral blood mononuclear cells are thawed, washed 2× in saline/PBS and resuspended at $5\times10^5$ cell/ml in RPMI/10% human AB serum. Cells are plated at 200:l/well. Heat inactivated KOS HSV-1 particles ($2\times10^5$ pfu per well) are added to the experimental wells. Concanavalin A (5:g/ml) is added to other wells as a positive control. Negative control wells have no additions. Plates are incubated at 37° C., 5% $CO_2$ for 5 days and then assayed for proliferation with Cell Counting Kit 8, a tetrazolium dye assay (Dojindo Molecular Technologies, Gaithersburg, Maryland).

Results are calculated by averaging optical density of the wells in each of the groups. A stimulation index is calculated to reflect the proliferation in the wells stimulated by killed HSV as compared to the positive and negative controls. The average optical absorbance of the positive controls is set as a stimulation index (SI) value of 100 and the average absorbance of the negative controls as a SI value of 0.

Results:

A total of 46 patients have been enrolled in the study and have not dropped out.

The groups are:

| Group name | Sensitization solution | Treatment solution |
|---|---|---|
| A (Placebo) | 0% SADBE in DMSO | 0% SADBE in DMSO |
| B | 2% SADBE in DMSO | 0.5% SADBE in DMSO |
| C | 2% SADBE in DMSO | 0.2% SADBE in DMSO |

Surprisingly, it was found that persons in the treatment groups B and C receiving 2% SADBE in DMSO as a sensitization dose usually did not have a subsequent outbreak during the study time, whereas those in the placebo group A usually did. This is shown in Table 16.

TABLE 16

Proportion of subjects in each treatment group having a cold sore outbreak within 120 days after receiving the sensitization dose.
Persons having an outbreak within X days after the sensitization dose

| | Group | | | | p value for A proportion versus B + C proportion |
|---|---|---|---|---|---|
| Days | A (Placebo) | B | C | B + C | |
| 30 days | 5 (of 15) | 2 (of 16) | 3 (of 15) | 5 (of 31) | 0.26 |
| 45 days | 8 (of 15) | 4 (of 16) | 4 (of 15) | 8 (of 31) | 0.099 |
| 60 days | 9 (of 15) | 5 (of 16) | 4 (of 15) | 9 (of 31) | 0.0583 |
| <120 days | 11 (of 15) | 6 (of 16) | 4 (of 15) | 10 (of 31) | 0.0125* |
| Total persons in group | 15 | 16 | 15 | 31 | |

*statistically significant (p < 0.05)
The p value was calculated using the Fischer's two-tailed exact test.

In addition, the proportion in group A who had a first outbreak between 30 and 120 days after receiving the sensitization dose was 4 of 14, while the proportion in pooled groups B and C was 5 of 26, and this difference is also statistically significant. (p<0.05). The average days to the first outbreak after the sensitization dose was also measured. If a patient had not had an outbreak by 120 days, a value of 120 days was used. The A: placebo, 0% SADBE in DMSO.

TABLE 17

Average days to first outbreak after the sensitization dose
(using 120 days if a subject has not had an outbreak in 120 days.)
Days to 1st outbreak

| | Group | | | |
|---|---|---|---|---|
| | A (Placebo) | B | C | B + C |
| Average | 63.0* | 88.5 | 94.7 | 91.5* |
| Standard deviation | 41.80 | 40.86 | 48.4 | 44.02 |
| n | 15 | 16 | 15 | 31 |
| <120 days | 11 (of 15) | 6 (of 16) | 4 (of 15) | 10 (of 31) |
| Total in study | 15 | 16 | 15 | 31 |

*statistically significant difference, p < 0.05, t test.

The difference in average days between group A (placebo) and the pooled groups B and C is statistically significant (p=0.041).

Table 18 shows the days to the first new outbreak from the date of the sensitization dose (2% SADBE or placebo applied to the inner aspect of the upper arm) in each patient.

TABLE 18

Days to first new outbreak after
sensitization dose on upper arm

| Placebo group | 2% SADBE |
|---|---|
| 19 | 14 |
| 20 | 14 |
| 24 | 15 |
| 25 | 18 |
| 28 | 34 |
| 40 | 37 |
| 40 | 41 |
| 42 | 50 |
| 56 | 80 |
| 64 | 91 |
| 98 | >120 |
| 107 | >120 |
| >120 | >120 |
| >120 | >120 |
| >120 | >120 |
| median = 42 days | >120 |
| | >120 |
| | >120 |
| | >120 |
| | >120 |
| | >120 |
| | >120 |
| | >120 |
| | >120 |
| | >120 |
| | >120 |
| | >120 |
| | median = greater than 120 days |

*Kaplan-Meier log rank P = 0.009

The median time to the next outbreak in the placebo group was 42 days, while in the treatment group it was greater than 120 days. The P value for the time to event by Kaplan-Meier log rank test was 0.009, a highly significant difference. If the outbreaks occurring in the 21 days after the sensitization dose are excluded, the median time to the next outbreak was 56 days in the placebo group and again over 120 days in the treatment group, counting from the day of the sensitization dose. Counting from day 21 after the sensitization dose, the median time to the next outbreak was 35 days (56 minus 21) for the placebo group and greater than 99 days for the treatment group.

Thus, a single sensitization dose of 2% SADBE in DMSO on the upper arm significantly reduced time to outbreaks and the proportion of persons who had an outbreak at all for at least 120 days. It prevented future outbreaks. This occurred even without a treatment dose applied to the lip during an outbreak.

Many of the subjects had a rash (erythema) from the sensitization dose, which was not expected. In the placebo group A, 2 of 13 had a rash, and in the pooled treatment groups B and C, 17 of 28 had a rash (not all subjects reported whether they had a rash or not, which is why the total number of subjects here differs from Tables 16 and 17).

All patents, patent applications, and other publications cited are incorporated by reference.

What is claimed is:

1. A method of treating a fungal infection comprising:
   applying a topical immunosensitizer to the skin or a mucous membrane of a person infected with a fungus and in recognized need of treatment for the fungal infection;
   wherein the applying step is done no more than 6 times in a 12 month period;
   wherein the topical immunosensitizer is squaric acid dibutyl ester (SADBE), a squaric acid ester, diphenyl-cyclopropenone (DPCP), 1-chloro-2,4-dinitrobenzene (DNCB), 1-chloro-2,6-dinitrobenzene, or urushiol;
   wherein if the fungal infection is an infection of the skin or mucous membrane the method does not comprise applying the topical immunosensitizer to at least some area or areas of diseased skin or diseased mucous membrane of the person arising from the fungal infection; and
   wherein the person is in recognized need of treatment for the fungal infection.

2. The method of claim 1 wherein the fungal infection is a yeast infection.

3. The method of claim 2 wherein the infection is a vaginal yeast infection.

4. The method of claim 1 wherein the person is in recognized need of treatment for oral thrush.

5. The method of claim 1 wherein the infection is an infection of the skin or mucous membrane or causes lesions on the skin or mucous membrane.

6. The method of claim 5 wherein the infection causes lesions on the skin and the applying step comprises applying the topical immunosensitizer to a skin lesion caused by the infection.

7. The method of claim 5 wherein the infection causes lesions on the skin and the applying step does not comprise applying the topical immunosensitizer to a skin lesion caused by the infection.

8. The method of claim 1 wherein the applying step is done no more than 4 times in a 12 month period.

9. The method of claim 1 wherein the method does not comprise any two incidences of the applying step within 6 weeks of each other.

10. The method of claim 1 wherein the topical immunosensitizer is squaric acid dibutyl ester (SADBE), a squaric acid ester, diphenylcyclopropenone (DPCP), 1-chloro-2,4-dinitrobenzene (DNCB), or 1-chloro-2,6-dinitrobenzene.

11. The method of claim 10 wherein the topical immunosensitizer is SADBE.

12. The method of claim 11 wherein the topical immunosensitizer is dissolved in dimethylsulfoxide (DMSO).

13. A method of treating molluscum contagiosum comprising:
   applying a topical immunosensitizer to the skin of a person infected with molluscum contagiosum pox virus and in recognized need of treatment for molluscum contagiosum;
   wherein the applying step is done no more than 6 times in a 12 month period and the method does not comprise any two incidences of the applying step within 6 weeks of each other;
   wherein the topical immunosensitizer is squaric acid dibutyl ester (SADBE); and
   wherein the method does not comprise applying the topical immunosensitizer to at least one or more molluscum contagiosum lesions of the person.

14. The method of claim 13 wherein the method comprises applying the topical immunosensitizer to a molluscum contagio sum skin lesion.

15. The method of claim 13 wherein the method does not comprise applying the topical immunosensitizer to a molluscum contagiosum skin lesion.

16. The method of claim 1 wherein the fungal infection is a *Candida albicans* infection.

17. The method of claim 13 wherein the topical immunosensitizer is dissolved in dimethylsulfoxide (DMSO).

* * * * *